(12) United States Patent
Stubiger et al.

(10) Patent No.: US 10,655,157 B2
(45) Date of Patent: May 19, 2020

(54) MICROBIAL ANALYSIS

(71) Applicant: KRATOS ANALYTICAL LIMITED, Manchester, Greater Manchester (GB)

(72) Inventors: Gerald Stubiger, Vienna (AT); Omar Belgacem, Salford (GB)

(73) Assignee: KRATOS ANALYTICAL LIMITED, Manchester, Greater Manchester (GB)

( * ) Notice: Subject to any disclaimer, the term of this patent is extended or adjusted under 35 U.S.C. 154(b) by 0 days.

(21) Appl. No.: 15/028,052

(22) PCT Filed: Oct. 9, 2014

(86) PCT No.: PCT/GB2014/053043
§ 371 (c)(1),
(2) Date: Apr. 8, 2016

(87) PCT Pub. No.: WO2015/052525
PCT Pub. Date: Apr. 16, 2015

(65) Prior Publication Data
US 2016/0237469 A1 Aug. 18, 2016

(30) Foreign Application Priority Data
Oct. 9, 2013 (GB) .................................. 1317837.1

(51) Int. Cl.
*C12Q 1/04* (2006.01)
*G01N 33/68* (2006.01)
(Continued)

(52) U.S. Cl.
CPC ........... *C12Q 1/04* (2013.01); *G01N 33/6851* (2013.01); *G01N 33/92* (2013.01); *H01J 49/0418* (2013.01)

(58) Field of Classification Search
None
See application file for complete search history.

(56) References Cited

U.S. PATENT DOCUMENTS

2004/0214259 A1 10/2004 Peacock et al.
2005/0035284 A1 2/2005 Schultz et al.
(Continued)

FOREIGN PATENT DOCUMENTS

CN 102033114 A 4/2011
CN 102706952 A 10/2012
(Continued)

OTHER PUBLICATIONS

Zhou, P., et al. Study of Matrix Additives for Sensitive Analysis of Lipid A by Matrix-Assisted Laser Desorption Ionization Mass Spectrometry, 2010, Applied and Environmental Microbiology, vol. 76(11), pp. 3437-3443.*
(Continued)

*Primary Examiner* — Xiaoyun R Xu
(74) *Attorney, Agent, or Firm* — Sughrue Mion, PLLC

(57) ABSTRACT

The present invention is concerned with a method of identifying microbial strains (e.g. from a cell culture), the method comprising; i) a lipid extraction step, comprising extraction of phospholipids from the microbe, suitably with an extraction composition comprising more than 50 vol % MeOH; ii) a sample preparation step, comprising preparation of a MALDI sample incorporating the extracted lipids; iii) a data gathering step, comprising performing MALDI-based mass spectrometry on the MALDI sample, and iv) a microbe identification step, comprising analysis of the mass spectrometry data to characterise or identify the microbial strain. Suitably the method also includes extracting proteins from the microbes and analysing the extracted proteins using MALDI-based mass spectrometry so as to obtain not only lipid m/z data but also protein m/z data.

20 Claims, 30 Drawing Sheets

(51) Int. Cl.
 G01N 33/92 (2006.01)
 H01J 49/04 (2006.01)

(56) References Cited

U.S. PATENT DOCUMENTS

| | | |
|---|---|---|
| 2007/0275478 A1 | 11/2007 | Taranenko et al. |
| 2008/0108104 A1 | 5/2008 | Eckstein et al. |
| 2008/0187907 A1 | 8/2008 | Bartholomew et al. |
| 2010/0116980 A1 | 5/2010 | Nassif et al. |
| 2012/0197535 A1 | 8/2012 | Goodlett et al. |
| 2013/0146758 A1 | 6/2013 | Urban et al. |

FOREIGN PATENT DOCUMENTS

| | | |
|---|---|---|
| DE | 100 38 694 A1 | 2/2002 |
| JP | 2007-309695 A | 11/2007 |
| WO | 2010/020812 A1 | 2/2010 |
| WO | 2012/016929 A1 | 2/2012 |

OTHER PUBLICATIONS

Vermillion-Salsbury, R. L. 9-Aminoacridine as a Matrix for negative mode matrix-assisted laser desorption/ionization, 2002, Rapid Communication in Mass Spectrmetry, vol. 16, pp. 1575-1581.*
Zhao, Z. et al. An extremely simple method for extraction of lysophospholipids and phospholipids from blood samples, 2010, Journal of Lipid Research, vol. 51, pp. 652-659.*
Xu, S. et al. Matrix with High Salt Tolerance for the Analysis of Peptide and Protein Samples by Desorption/Ionization Time-of-Flight Mass Spectrometry, Analytical Chemistry, vol. 78, pp. 2593-2599 (Year: 2006).*
Powell, D.W. et al. Cluster Analysis of Mass Spectrometry Data Reveals a Novel Component of SAGA, Molecular and Cellular Biology, vol. 24(6), pp. 7249-7259 (Year: 2004).*
Vitali Matyash et al., "Lipid extraction by methyl-tert-butyl ether for high-throughput lipidomics", Journal of Lipid Research, 2008, pp. 1137-1146, vol. 49.
Ying S. Ting et al., "Automated Lipid A Structure Assignment from Hierarchical Tandem Mass Spectrometry Data", J. Am. Soc. Mass Spectrom., 2011, pp. 856-866, vol. 22.
Asmaa El Hamidi et al., "Microextraction of bacterial lipid A: easy and rapid method for mass spectrometric characterization", Journal of Lipid Research, 2005, pp. 1773-1778, vol. 46.
Xi Shu et al., "Rapid lipid profiling of bacteria by online MALDI-TOF mass spectrometry", International Journal of Mass Spectrometry, 2012, pp. 71-76, vol. 321-322.
Gang Sun et al., "Matrix-Assisted Laser Desorption/Ionization Time-of-Flight Mass Spectrometric Analysis of Cellular Glycerophospholipids Enabled by Multiplexed Solvent Dependent Analyte-Matrix Interactions", Anal. Chem., 2008, pp. 7576-7585, vol. 80.
Gerald Stübiger et al., "Analysis of Oxidized Phospholipids by MALDI Mass Spectrometry Using 6-Aza-2-thiothymine Together with Matrix Additives and Disposable Target Surfaces ", Anal. Chem., 2010, pp. 5502-5510, vol. 82.
Jennifer Gidden et al., "Lipid compositions in Escherichia coli and Bacillus subtilis during growth as determined by MALDI-TOF and TOF/TOF mass spectrometry", International Journal of Mass Spectrometry, 2009, pp. 178-184, vol. 283.
Gerald Stübiger et al., "Analysis of Lipids Using 2,4,6-Trihydroxyacetophenone as a Matrix for MALDI Mass Spectrometry", Anal. Chem., 2007, pp. 3206-3213, vol. 79.
Zhenwen Zhao et al., "An extremely simple method for extraction of lysophospholipids and phospholipids from blood samples", Journal of Lipid Research, 2010, vol. 51.
James P. Nataro et al., "Diarrheagenic Escherichia coli", Clinical Microbiology Reviews, Jan. 1998, pp. 142-201, vol. 11, No. 1.
Oksana Lukjancenko et al., "Comparison of 61 Sequenced Escherichia coli Genomes", Microb Ecol, 2010, pp. 708-720, vol. 60.
Teresa C. Cain et al., "Differentiation of Bacteria Using Protein Profiles from Matrix-assisted Laser Desorption/Ionization Time-of-flight Mass Spectrometry", Rapid Communications in Mass Spectrometry, 1994, pp. 1026-1030, vol. 8.
Alex Van Belkum et al., "Biomedical Mass Spectrometry in Today's and Tomorrow's Clinical Microbiology Laboratories", Journal of Clinical Microbiology, 2012, pp. 1513-1517, vol. 50, No. 5.
John P. Anhalt et al., "Identification of Bacteria Using Mass Spectrometry", Analytical Chemistry, Feb. 2, 1975, pp. 219-225, vol. 47, No. 2.
Gregory E. Sims et al., "Whole-genome phylogeny of Escherichia coli/Shigella group by feature frequency profiles (FFPs)", PNAS Early Edition, pp. 1-6.
Elzbieta Brzuszkiewicz et al., "Genome sequence analyses of two isolates from the recent Escherichia coli outbreak in Germany reveal the emergence of a new pathotype: Entero-Aggregative-Haemorrhagic Escherichia coli (EAHEC)", Arch Microbiol, 2011, pp. 883-891, vol. 193.
Martin A. Claydon et al., "The rapid identification of intact microorganisms using mass spectrometry", Nature Biotechnology, Nov. 1996, pp. 1584-1586, vol. 14.
Cosima D. Calvano et al., "Lipid fingerprinting of Gram-positive lactobacilli by intact cells—matrix-assisted laser desorption/ionization mass spectrometry using a proton sponge based matrix", Rapid Commun. Mass Spectrom., 2011, pp. 1757-1764, vol. 25.
Marta Palusinska-Szysz et al., "Legionella bozemanae synthesizes phosphatidylcholine from exogenous choline", Microbiological Research, 2011, pp. 87-98, vol. 166.
Yanyan Li et al., "A rapid one-step method for the characterization of membrane lipid remodeling in Francisella using matrix-assisted laser desorption ionization time-of-flight tandem mass spectrometry", Rapid. Commun. Mass Spectrom., 2011, pp. 2641-2648, vol. 25.
Erin Maloney et al., "The Two-Domain LysX Protein of Mycobacterium tuberculosis is Required for Production of Lysinylated Phosphatidylglycerol and Resistance to Cationic Antimicrobial Peptides", PLoS Pathogens, Jul. 2009, pp. 1-13, vol. 5, Issue 7.
S. Mariccor A.B. Batoy et al., "Lipid and Phospholipid Profiling of Biological Samples Using MALDI Fourier Transform Mass Spectrometry", Lipids, 2009, pp. 367-371, vol. 44.
Jackson O. Lay, Jr. "Characterization of Lipids by MALDI Mass Spectrometry", The AOCS Lipid Library, 7 pgs., Available at http://lipidlibrary.aocs.org/lipidomics/maldi-lay/index.htm.
Rachal L. Vermillion-Salsbury et al., "9-Aminoacridine as a matrix for negative mode matrix-assisted laser desorption-ionization", Rapid Communications in Mass Spectrometry, 2002, pp. 1575-1581, vol. 16.
Jiang Qian et al., "MALDI-TOF mass signatures for differentiation of yeast species, strain grouping and monitoring of morphogenesis markers", Anal. Bioanal Chem., pp. 439-449, vol. 392.
Roberto Angelini et al., "MALDI-TOF/MS analysis of archaebacterial lipids in lyophilized membranes dry-mixed with 9-aminoacridine", Journal of Lipid Research, 2010, pp. 2818-2825, vol. 51.
Rishi Singhal et al., "MALDI profiles of proteins and lipids for the rapid characterisation of upper GI-tract cancers", Journal of Protoemics, 2013, pp. 207-215, vol. 80.
UK Search Report for GB1317837.1 dated Jun. 23, 2014.
UK Search Report for GB1417899.0 dated Jul. 31, 2015.
International Search Report for PCT/GB2014/053043 dated Jan. 12, 2015.
Written Opinion for PCT/GB2014/053043 dated Jan. 12, 2015.
C.D. Calvano et al., "1,8-Bis(dimethylamino)naphthalene/9-aminoacridine: A new binary matrix for lipid fingerprinting of intact bacteria by matrix assisted laser desorption ionization mass spectrometry", Analytica Chimica Acta, 2013, pp. 56-63, vol. 798.
S. G. Batrakov et al., "Unusual fatty acid composition of cerebrosides from the filamentous soil fungus Mortierella alpine", Chemistry and Physics of Lipids, 2002, vol. 117, pp. 45-51.
Anne M. Distler et al., "Mass spectrometric detection of protein, lipid and heme components of cytochrome c oxidase from R. sphaeroides and the stabilization of non-covalent complexes from the enzyme", Eur. J. Mass Spectrom., 2004. pp. 295-308, vol. 10.

(56) References Cited

OTHER PUBLICATIONS

Karlheinz Grillitsch et al., "Lipid particles/droplets of the yeast Saccharomyces cerevisiae revisited: Lipidome meets Proteome", Biochimica et Biophysica Acta, 2011, vol. 1811, pp. 1811 11651176.

Suresh Kumar Kailasa et al., "Surface modified BaTiO3 nanopartides as the matrix for phospholipids and as extracting probes for LLME of hydrophobic proteins in Escherichia coli by MALDI-MS", Talanta, 2013, vol. 114, pp. 283-290.

Jeffrey J. Jones et al., "Investigation of MALDI-TOF and FT-MS techniques for analysis of *Escherichia coli* whole cells", Analytical Chemistry, 2003, vol. 75, pp. 1340-1347.

John D. Leszyk, "Evaluation of the New MALDI Matrix 4-Chloro-a-Cyanocinnamic Acid", Journal of Biomolecular Techniques, 2010, vol. 21, pp. 81-91.

R. Vitale et al., "Lipid fingerprints of intact viruses by MALDI-TOF/mass spectrometry" Biochimica et Biophysica Acta, 2013, vol. 1831, pp. 872-879.

Justin M. Hettick et al., "Proteomic Profiling of Intact Mycobacteria by Matrix-Assisted Laser Desorption/Ionization Time-of-Flight Mass Spectrometry", Analytical Chemistry, 2004, vol. 76, pp. 5769-5776.

\* cited by examiner

E. coli
(-)MALDI
Resonance
MS2

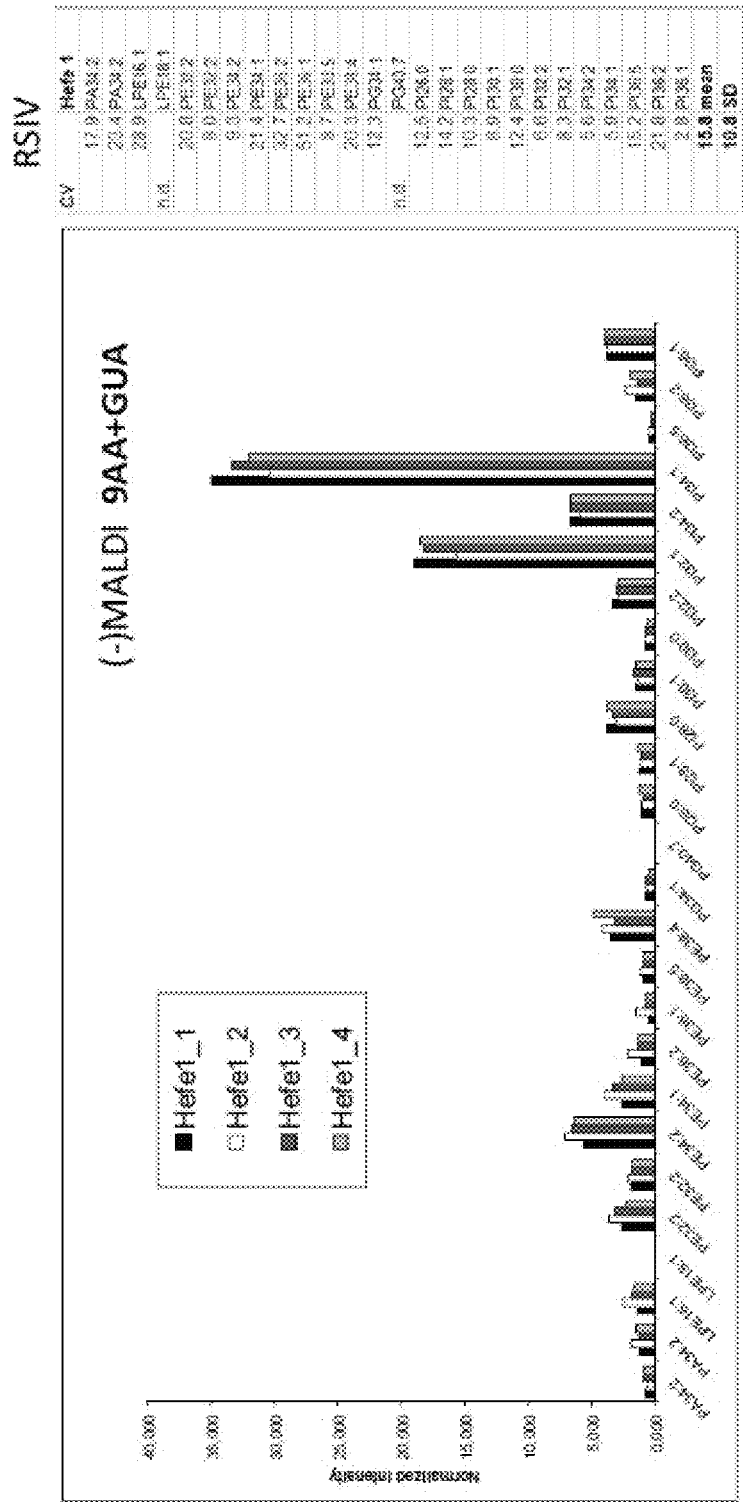
Figure 12C (A)

| Extraction | % (ID) | family | genus | species | strain | typ | data count (SCORE) |
|---|---|---|---|---|---|---|---|
| MeOH | 99.9 | Family: Enterobacteriaceae | Klebsiella | pneumoniae | | | 162 |
| MeOH | 99.9 | Family: Enterobacteriaceae | Klebsiella | pneumoniae | | | 175 |
| MeOH | 99.9 | Family: Enterobacteriaceae | Klebsiella | pneumoniae | | | 173 |
| MeOH | 99.9 | Family: Enterobacteriaceae | Klebsiella | pneumoniae | | | 168 |
| MeOH | 99.9 | Family: Enterobacteriaceae | Escherichia | coli | DH5D | | 198 |
| MeOH | 99.9 | Family: Enterobacteriaceae | Escherichia | coli | DH5D | | 193 |
| MeOH | 99.9 | Family: Enterobacteriaceae | Escherichia | coli | DH5D | | 204 |
| MeOH | 99.9 | Family: Enterobacteriaceae | Escherichia | coli | DH5D | | 212 |
| | Mean | | | | | | 187.3 |
| | SD | | | | | | SD 17.4 |
| | 99.9 | | RSD(%) | 0.0 | | | RSD(%) 9.3 |

(B)

| Extraction | % (ID) | family | genus | species | strain | typ | data count (SCORE) |
|---|---|---|---|---|---|---|---|
| na | 75.2 | Family: Enterobacteriaceae | Klebsiella | pneumoniae | | | 187 |
| na | 99.9 | Family: Enterobacteriaceae | Klebsiella | pneumoniae | | | 125 |
| na | | | | | | | 98 |
| na | 87.6 | Family: Enterobacteriaceae | Escherichia | coli | DH5D | | 126 |
| na | 97.4 | Family: Enterobacteriaceae | Escherichia | coli | DH5D | | 128 |
| na | 99.9 | Family: Enterobacteriaceae | Escherichia | coli | DH5D | | 174 |
| na | 99.9 | Family: Enterobacteriaceae | Escherichia | coli | DH5D | | 159 |
| | | | | | | | 168 |
| | Mean | | | | | | 135.8 |
| | SD 82.5 | | | | | | SD 28.4 |
| | | | RSD(%) | 41.8 | | | RSD(%) 20.9 |

(A) Blue: SARAMIS results after MeOH extraction of the cells from cell culture (agar plate)
(B) Red: SARAMIS results directly from cell culture (no MeOH extraction)
Mean ± standard deviation (SD) of four replicate sample analyses of each species are displayed
ID represents the confidence level of identification (%) and the data count (SCORE) represents the number of positively identified peaks per spectrum

Figure 16

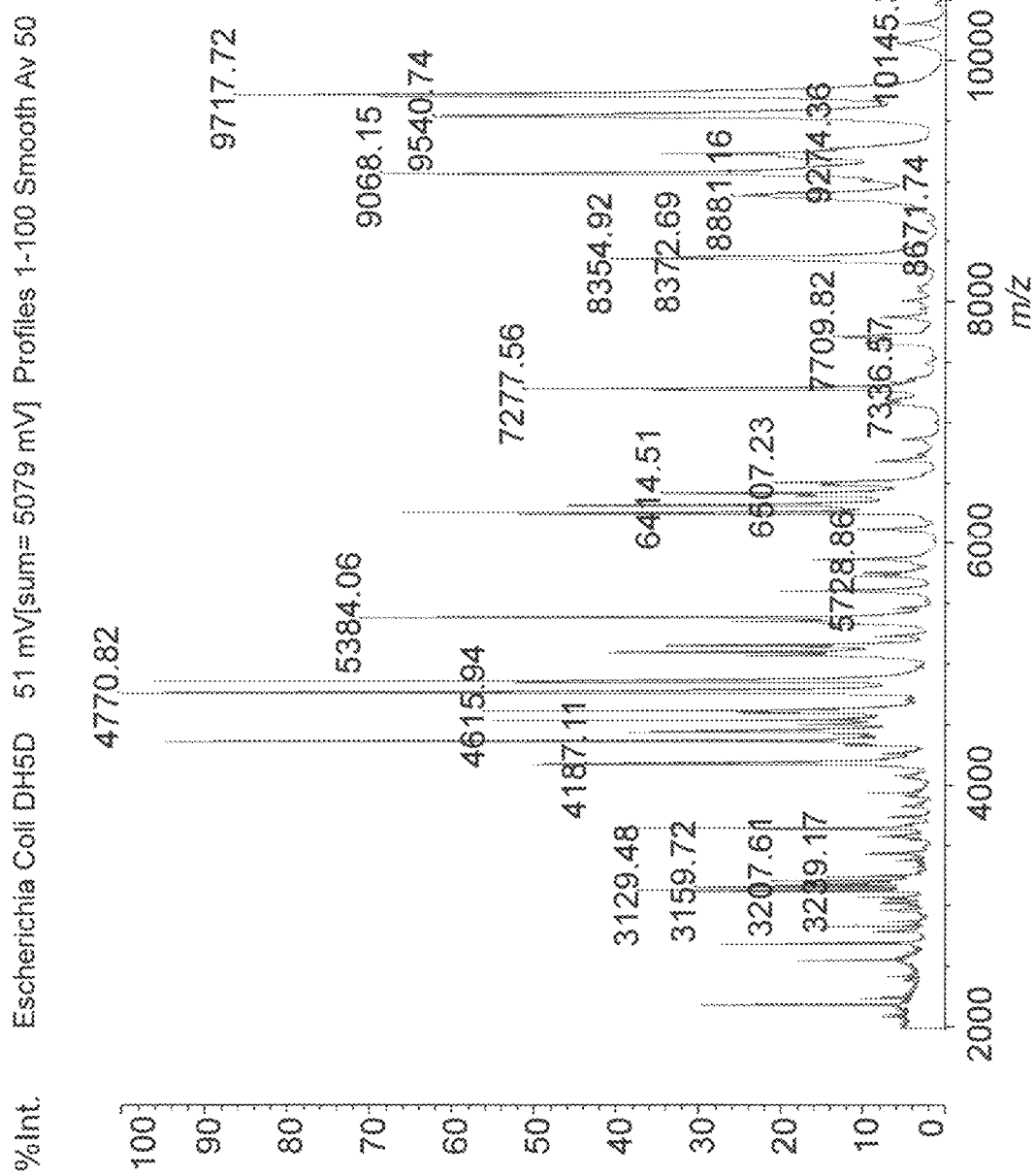

MICROBIAL ANALYSIS

FIELD

The present invention relates to a method of analysing microbes. The analysis is based on lipid profiling, and can be used in microbial identification.

BACKGROUND

It is desirable to swiftly and simply, reliably identify microbes. Reliable identification allows the pathogenicity and/or other characteristics of a microbial sample to be identified. Determining the biomolecule make-up of a microbe can assist in identification and hence diagnosis.

Mass spectrometry can be used to analyse biomolecules, typically using soft ionization techniques. Matrix-Assisted Laser Desorption/Ionization (MALDI)-MS is one such technique, and has been widely used in the analysis of large biomolecules including proteins. Protein fingerprinting has enabled the application of MALDI-MS for microbial identification and diagnostics.

However, protein fingerprinting cannot reliably differentiate between different strains of the same species. Serological testing or PCR analysis is needed to test the pathogenicity of a sample.

Lipids are known to be structurally important within cells, and are the major components of cell membranes and other sub-cellular structures. They are active in major cellular mechanisms, and influence the properties and functionality of proteins.

US 2012/0197535 describes glycolipid (saccharolipid) extraction from bacterial samples. Analysis of the glycolipid make-up using mass spectrometry techniques (including MALDI) allows identification of bacterial strains. This technique exploits the specificity of bacterial outer cell wall glycolipid structures (e.g. Lipid A, lipoteichoic acid). However, this method was developed for and tailored to the specific extraction of these glycolipids and the inventors have found that it is not widely applicable. For example, it cannot be used to determine the identity of other microbial organisms (e.g. yeasts or fungi), which do not contain these glycolipids.

The cellular structure of microbes can vary greatly between different genera (e.g. bacteria, yeast, filamentous fungi), and even within a genus at the species level. For example, prokaryotic organisms (e.g. bacteria) are divided into two major groups, Gram+ and Gram−, depending on the characteristics of their cell structures. However, despite the quite different architecture of the cell structures in prokaryotes and eukaryotes (e.g. yeasts and fungi), all have a cytoplasmic membrane.

Phospholipids (PLs) (particularly glycerophospholipids and phosphosphingolipids) are known to be the major membrane lipids of many microbes. Indeed, components of phospholipid biosynthesis and the PLs themselves are membrane bound and serve as the precursors of other cell membrane components.[1]

For example, cationic phosphatidylcholine (PC) accounts for about 50% of total membrane lipids in eukaryotes alongside phosphatidylserine (PS) and phosphatidylinositol (PI) as minor components. Zwitterionic phosphatidylethanolamine (PE), anionic phosphatidylglycerol (PG) and/or cardiolipin (CL) represent the major membrane lipids of most known bacteria (e.g. up to 80% PE in *E. coli*).[2] Other significant PLs are amino acid esters of PG (e.g. lysyl -, alanyl-,or ornithyl-PG)[14].

Some other neutral lipids (NLs) (or non-polar lipids), such as diacylglycerols (DAGs), triacylglycerols (TAGs) and cholesteryl esters (CEs), are known to also play an important role in cell membrane functionality. Although CEs are only rarely found in prokaryotes (i.e. bacteria) they are more common lipid components of eukaryotes (i.e. yeasts, fungi and mammalian cells). These lipid molecules contain 1-3 fatty acids esterified to a glycerol or sterol backbone. A significant group of NLs is the glycosyl diglycerides (e.g. digalactosyldiglyceride, DGDG), which are found mainly in Gram+ bacteria (e.g. *Bacillus* spp.)[14].

The importance of PLs (and NLs) for cell membranes, means that homeostasis of the lipid composition is very important to sustain the cell membrane integrity and functionality (e.g. trans-membrane signalling, intercellular interactions, energy metabolism, cell proliferation, etc.) of microbial cells and their viability in different environments.[3] It is well known that alterations to cellular PL compositions can result from exposure of microbes to environmental stresses, such as extreme temperatures, toxic substances, food additives and antibiotics.[4][5][6][7]

Consequently, microbial cells possess a very characteristic, evolutionary based phospholipid composition that can be used for chemotaxonomic purposes, whereby small differences in the phospholipid profiles can potentially be exploited for differentiation at the strain level. This allows for strains with certain characteristics to be identified, including those that are pathogenic and resistant to antibiotics.

Microbial phospholipid compositions are very complex, and are typically analysed using mass spectrometry (MS) because it allows the simultaneous detection of many individual molecular species within a single MS spectrum. One of the first examples of using MS for the classification of microorganisms was the use of gas-chromatography (GC)-MS.[8] GC-MS is used for cellular fatty acid analysis because of its good chromatographic separation potential.[9] However, lipids need to be broken down into constituent fatty acid molecules to be analysed, and thus the phospholipid composition within the cells cannot be determined.

Functional analysis of phospholipids suggests that the structural properties (e.g. head group, chain length, degree of unsaturation) are primarily responsible for membrane function.[10] This information is also lost when phospholipids are broken down into their constituent fatty acids.

Accordingly, detection techniques conserving intact phospholipid structures during analysis are more appropriate for chemotaxonomical purposes. Some reports have shown the usefulness of intact lipid profiling for differentiation of bacteria using softer-ionisation techniques like fast-atom bombardment (FAB)[11] and electrospray ionization (ESI)-MS.[12]

However, MALDI-MS is generally a preferred soft-ionisation technique. Data can be obtained simply and quickly, and is relatively simple to analyse because the molecules are almost exclusively detected as singly charged ions upon laser irradiation of the matrix-embedded samples. Further the instruments used are robust and reliable allowing the analysis of crude (i.e. unpurified) samples. Consequently, MALDI-MS has developed into a routine technique for microbial diagnostics based on "protein fingerprinting".[13]

Recently, MALDI-MS has been reported as a method for bacterial phospholipid analysis.[14][15] However, a lack of reliable sample preparation protocols and instrumentation techniques has prevented wider application of these methods. Routine bacterial identification by phospholipid analysis using MALDI-MS has not been possible for closely related bacteria, preventing its use in taxonomy. Moreover, no successful lipid MALDI-MS analysis has been reported for other types of microbe (e.g. yeasts and fungi), which must still be identified by cell morphology using light microscopy, genotyping, and/or protein fingerprinting.

Furthermore, differentiation of microbial strains (within a species) using MALDI-MS based phospholipid profiling has not been reported. Nor has MALDI-MS based lipid profiling of yeasts or fungi.

SUMMARY OF THE INVENTION

At its most general, the present invention provides a method of microbial analysis that can differentiate microbial strains based on the constituent lipid analysis. The methods use MALDI mass spectrometry. In some cases, the method analyses microbial phospholipids. Optionally the method also analyses microbial proteins. Thus, "protein fingerprinting" and "lipid fingerprinting" can be performed on the same microbes. Indeed, the same extraction process can be used to obtain extracted lipids and extracted proteins. This facilitates subsequent MALDI-MS analysis, and that analysis can include merging the data from lipid and protein m/z ranges.

The data from this analysis can be used to simply and reliably identify microbial strains.

In a first aspect, the invention provides a method of identifying microbial strains, the method comprising;
   i) a lipid extraction step, comprising extraction of phospholipids from the microbe;
   ii) a sample preparation step, comprising preparation of a MALDI sample incorporating the extracted phospholipids; and
   iii) a data gathering step, comprising performing MALDI-based mass spectrometry on the MALDI sample,
   iv) a microbe identification step, comprising analysis of the mass spectrometry data to characterise or identify the microbial strain.

In contrast to prior art methods, microbes can be identified at the strain level. Similar, closely-related microbes can be differentiated using the method devised by the inventors.

An early process for bacterial identification by lipid profiling described in the prior art[14] indicates that lipid "composition and relative amounts in a given bacterium are dependent on environmental conditions", and that "this may cause difficulty in using lipid profiles for taxonomy and for differentiating very similar bacterial species". Lipid analysis, it states, can be used "in differentiating bacteria in significantly different groups such as a Gram-positive from a Gram-negative bacterium."

Further work in this area also notes the variation in lipid compositions arising from environmental conditions, such as culture[15] This further work has sought to improve the earlier methods focused on different protocols to speed up bacterial identification.

In contrast to the prior art, the inventors have found that lipid profiling can be used to identify microbial strains. The inventors have determined that lipid profiles recorded from bacterial cell cultures at certain time points (e.g. after 24 or 72 hours) or using certain culture media (e.g. blood or minimal agar) allow reliable differentiation of bacterial stains. Consequently, the presently claimed method allows chemotaxonomic identification at the sub-species level, and has been devised to increase the signal to noise ratio and mass spectral reproducibility, amongst other factors.

The claimed method is simple, fast, easy and reliable.

The method is particularly useful in the clinical/hospital environment where very large numbers of tests (to identify microbe information) are carried out and it is important to have high confidence in the result.

As is discussed in more detail below, suitably the method includes obtaining mass spectrometry data for proteins as well as for lipids (e.g. phospholipids). That is, suitably the method includes "protein fingerprinting" as well as "lipid fingerprinting" so as to differentiate microbial strains.

The inventors have found that a single extraction step can facilitate extraction of both lipids (suitably including phospholipids) and proteins. As described in embodiments herein, the extracted material containing lipids and proteins can be used, with suitable matrices, for both lipid analysis (typically m/z=100 to 3000, e.g. 200 to 2000) and protein analysis (typically m/z =2000 to 20000). This "all-in-one" approach provides a reliable, simple, quick and cost effective method for accessing valuable sub-species information.

Suitably extraction step i) includes extraction of proteins from the microbe. Suitably lipids and proteins are extracted using the same extraction composition (e.g. MeOH or MeOH/$H_2O$). As discussed below, this facilitates high throughput analysis because only one extraction composition is required in order to access both lipid information and protein information.

Suitably sample preparation step ii) includes a) preparation of a MALDI sample incorporating the extracted lipids, and b) preparation of a MALDI sample incorporating the extracted proteins. Typically steps ii) a) and ii) b) use different MALDI matrix materials.

Suitably data gathering step iii) includes obtaining mass spectrum data for the extracted lipids and obtaining mass spectrum data for the extracted proteins. In embodiments, the mass spectrum data for the lipids and the mass spectrum data for the proteins can be combined/merged.

In a second aspect, the invention provides a method of analysing microbes, the method comprising;
   i) a lipid extraction step, comprising extraction of lipids from the microbe;
   ii) a sample preparation step, comprising preparation of a MALDI sample incorporating the extracted lipids; and
   iii) a data gathering step, comprising performing MALDI-based mass spectrometry on the MALDI sample.

The second aspect allows different spectra to be obtained for different microbes.

In the same way as for the first aspect, suitably extraction step i) includes extraction of proteins from the microbe. Suitably the lipids and the proteins are extracted using the same extraction composition.

And similarly the sample preparation step ii) may include a) preparation of a MALDI sample incorporating the extracted lipids and, b) preparation of a MALDI sample incorporating the extracted proteins. Typically steps ii) a) and ii) b) use different MALDI matrix materials.

Again, suitably data gathering step iii) includes obtaining mass spectrum data for the extracted lipids and obtaining mass spectrum data for the extracted proteins. In embodiments, the mass spectrum data for the lipids and the mass spectrum data for the proteins can be combined/merged.

In a third aspect, the invention provides a method of analysing microbes, the method comprising;
   i) a lipid extraction step, comprising addition of a extraction composition to the microbes to extract lipids, wherein the extraction composition comprises more than 50 vol % alcohol or more than 50 vol % ether;
   ii) a sample preparation step, comprising preparation of a MALDI sample incorporating the extracted lipids; and
   iii) a data gathering step, comprising performing MALDI-based mass spectrometry on the MALDI sample.

The alcohol or ether based solvents used in the third aspect allows lipid MS spectra to be obtained, in which sub-species resolution can be reliably achieved for all microbe types. Preferably, the extraction composition comprises more than 50 vol % alcohol.

In contrast, the prior art methods[14][15], use Folch reagents for phospholipid extraction. [Folch reagents comprise $CHCl_3$ and MeOH in a volume ratio of from 3:1 to 1:1.] The Folch method is the most commonly used lipid extraction technique in the field of lipid analysis. However, the inventors have found that the resultant MALDI spectra are not reproducible, and that the small differences between the spectra of sub-species cannot be detected. The alcohol-based solvent extraction technique required in the third aspect improves the reproducibility of the mass spectra, and the background noise is low. Accordingly, sub-species resolution is possible. Surprisingly, this is also achieved when not only lipid analysis but also protein analysis is carried out. Thus, the tailored solvent system of the third aspect suitably provides low background noise and good reproducibility even when the m/z range includes both lipids (typically m/z=100 to 3000, for example 200 to 2000) and proteins (typically m/z=2000 to 20000).

US 2012/0197535 uses Folch reagents to extract glycolipids, and describes subsequent sub-species differentiation. However, as discussed above, glycolipids are not present in all microbes. The inventors' alcohol-based solvent extraction has been designed to allow the extraction of lipids from all microbes, wherein the MS spectrum of the extracted lipids allows subsequent sub-species resolution.

Further, the alcohol-based solvent used in the lipid extraction step will also dissolve the matrix material to allow sample preparation. This avoids the need for extra reagents, which reduces the cost, and results in a cleaner, more reproducible spectrum in which sub-species can be differentiated. In other words, the alcohol-based solvents used in the lipid extraction are much more compatible with the matrix materials than the Folch reagents.

It can be seen from FIG. 2 that use of the Folch reagents returns a mass spectrum with a very poor signal to noise (S/N) ratio, because the Folch reagents (especially $CHCl_3$) are less compatible with MALDI matrix materials. The noise level is such that sub-species resolution is not possible.

In a preferred case, the lipid extraction step extracts phospholipids. The alcohol-based solvent used in the extraction step has been specifically tailored to this end, i.e. to allow phospholipid extraction, in such a manner as to allow sub-species resolution.

As noted above, the tailored solvent system is not only effective to extract lipids (especially phospholipids) but also proteins. This permits protein fingerprinting and lipid fingerprinting using the same extract.

In the same way as for the first aspect, suitably extraction step i) includes extraction of proteins from the microbe. Suitably the lipids and the proteins are extracted using the same extraction composition. Optionally the extraction step i) includes adding water to the microbes (e.g. to the culture). This can be a precursor step before the addition of the extraction composition. Alternatively or additionally the extraction composition may comprise water. For example, an alcohol/water or ether/water mixture can be used. In embodiments, water is added to the microbes in a first (precursor) step followed by addition of alcohol (suitably methanol) in a second step.

And similarly, sample preparation step ii) may include a) preparation of a MALDI sample incorporating the extracted lipids and, b) preparation of a MALDI sample incorporating the extracted proteins. Typically steps ii) a) and ii) b) use different MALDI matrix materials.

Again, suitably data gathering step iii) includes obtaining mass spectrum data for the extracted lipids and obtaining mass spectrum data for the extracted proteins. In embodiments, the mass spectrum data for the lipids and the mass spectrum data for the proteins can be combined/merged.

In a fourth aspect the invention provides a method of analysing microbes, the method comprising;
i) a lipid extraction step, comprising extraction of lipids from the microbe;
ii) a sample preparation step, comprising preparation of a MALDI sample incorporating the extracted lipids; and
iii) a data gathering step, comprising performing MALDI-based mass spectrometry on the MALDI sample,
wherein;
the lipid extraction step comprises addition of a methanol solution or a methanol/acetone mixture to the microbes, and/or
the sample preparation step comprises addition of 9AA or ATT matrix material to the extracted lipids, and/or
in the data gathering step, the m/z range scanned is from about 100 to about 3000 in the MS1 spectrum.

In the same way as for the first aspect, suitably extraction step i) includes extraction of proteins from the microbe. Suitably the lipids and the proteins are extracted using the same extraction composition.

As discussed herein, the (lipid and protein) extraction step may comprise addition of water and alcohol (suitably selected from methanol or ethanol, preferably methanol), sequentially (suitably water first) or as a water-alcohol mixture.

And similarly, sample preparation step ii) may include a) preparation of a MALDI sample incorporating the extracted lipids and, b) preparation of a MALDI sample incorporating the extracted proteins. Typically steps ii) a) and ii) b) use different MALDI matrix materials. In embodiments, CHCA matrix material is used for the extracted proteins. That is, the sample preparation step (e.g. step ii) b)) includes addition of CHCA matrix material to the extracted proteins.

Again, suitably data gathering step iii) includes obtaining mass spectrum data for the extracted lipids and obtaining mass spectrum data for the extracted proteins. In embodiments, the mass spectrum data for the lipids and the mass spectrum data for the proteins can be combined/merged.

These methods allow highly reproducible, low noise, high information content lipid spectra to be obtained. The spectra of closely related microbes, including separate strains of the same species, can thus be differentiated. In a preferred case, the lipid extraction step extracts at least phospholipids.

In embodiments, the data gathering step further includes scanning in the m/z range from about 2000 to about 20000 in the MS1 spectrum. Thus, suitably the m/z range scanned is for protein analysis as well as for lipid analysis.

As discussed herein, the data gathering step may include 1) performing MALDI-MS on the MALDI sample prepared according to step ii) a), and 2) performing MALDI-MS on the MALDI sample prepared according to step ii) b). Thus, in embodiments, the same microbe sample is processed (extraction, MALDI sample preparation) so as to obtain m/z data for both lipid composition and for protein composition. This permits even higher confidence and reliability in the assignment of sub-species information for a microbe (e.g. a culture).

In a fifth aspect, the invention provides a method of analysing non-bacterial microbes, the method comprising;

i) a lipid extraction step, comprising extraction of lipids from the microbe;
ii) a sample preparation step, comprising preparation of a MALDI sample incorporating the extracted lipids; and
iii) a data gathering step, comprising performing MALDI-based mass spectrometry on the MALDI sample.

In the same way as for the first aspect, suitably extraction step i) includes extraction of proteins from the microbe. Suitably the lipids and the proteins are extracted using the same extraction composition.

And similarly, sample preparation step ii) may include a) preparation of a MALDI sample incorporating the extracted lipids and, b) preparation of a MALDI sample incorporating the extracted proteins. Typically steps ii) a) and ii) b) use different MALDI matrix materials.

Again, suitably data gathering step iii) includes obtaining mass spectrum data for the extracted lipids and obtaining mass spectrum data for the extracted proteins. In embodiments, the mass spectrum data for the lipids and the mass spectrum data for the proteins can be combined/merged.

In a sixth aspect, the invention provides a method of analysing microbes, the method comprising;
i) an extraction step, comprising extraction of lipids and proteins from the microbes;
ii) a sample preparation step, comprising preparation of one or more MALDI samples incorporating the extracted lipids and/or the extracted proteins; and
iii) a data gathering step, comprising performing MALDI-based mass spectrometry on the one or more MALDI sample(s) so as to obtain mass spectrometry data on the lipid composition of the microbes and on the protein composition of the microbes.

In embodiments, the mass spectrum data for the lipids and the mass spectrum data for the proteins can be combined/merged.

Suitably, the method includes iv) a microbe identification step, comprising analysis of the mass spectrometry data to characterise or identify the microbe, preferably the microbial strain. Suitably any such analysis is performed on the merged mass spectrum data.

As discussed herein, the sample preparation step ii) typically includes preparing one MALDI sample for protein analysis (using e.g. CHCA as matrix material) and one (a different) MALDI sample for lipid analysis (using e.g. ATT or 9AA as matrix material). Suitably the composition (typically a suspension) obtained from the extraction step is used to prepare both the MALDI sample for protein analysis (e.g. by addition of a suitable matrix material such as CHCA) and the MALDI sample for lipid analysis (e.g. by addition of a suitable matrix material such as ATT or 9AA).

Preferably, in each of the above aspects of the invention, the lipid extraction step comprises extraction of phospholipids. In some cases, at least about 20 vol %, preferably 40 vol %, 50 vol %, 60 vol %, 70 vol % or 80 vol % of the extracted lipids are phospholipids. In some cases, at least about 20 vol %, preferably 40 vol %, 60 vol % or 80 vol % of phospholipids in the sample are extracted.

Preferably, in each of the above aspects of the invention, the lipid extraction step comprises extraction of proteins.

Preferably, in each of the above aspects of the invention, the data gathering step includes obtaining mass spectrum data for lipids (typically by scanning in the m/z range 100 to 3000, for example 200 to 2000) and for proteins (typically by scanning in the m/z range 2000 to 20000), Optionally, the method of the second, third, fourth and fifth aspects may further comprise a microbe identification step, comprising analysis of the mass spectrometry data to characterise or identify the microbe. Optionally, the microbe identification step includes analysis of protein mass spectrometry data (typically including data obtained from some or all of the m/z range 2000 to 20000) as well as analysis of lipid mass spectrometry data (typically including data obtained from some or all of the m/z range 100 to 3000, typically 200 to 2000). By using both lipid m/z data and protein m/z data the present inventors have found that identification of microbe species and sub-species information is more reliable and there is a higher confidence in the information. This is particularly relevant for clinics/hospitals where diagnosis and subsequent treatment may be based on this information.

Optionally, the method of any aspect may further comprise a further, initial, microbe cultivation step.

A further aspect of the inventions pertains to a kit for implementing a method of any previous aspect. The kit comprises reagents necessary to implement the method, and a detailed protocol explaining each step in the method.

Suitably the kit comprises one or more of:
(i) a MALDI matrix material, and optionally a co-matrix material,
(ii) a sample plate,
(iii) a calibration mixture of cationic and anionic PL standards (suitably lyophilized), and
(iv) a set of instructions for completing a method as described herein.

Preferably the matrix material is selected from ATT, THAP and 9AA. and/or the optional co-matrix material is selected from DAHC, GUA and sodium or lithium acetate, and/or two or more sample plates (e.g. 16 sample plates) are included, wherein each is a 48-well target slide (e.g. Flexi-Mass™-DS target slide), and/or organic solvents for lipid extraction and/or matrix material dissolution are included.

In respect of embodiments where proteins are extracted and analysed, the MALDI matrix material is suitably selected from α-Cyano-4-hydroxycinnamic acid (CHCA), sinapinic acid (SA) and ferulic acid (FA). CHCA is preferred. Thus, the kit can include a first matrix material for lipid analysis, and a second matrix material (different from the first matrix material) for protein analysis.

Suitably the kit includes a container or enclosure in which the reagents and/or other components are located.

Throughout this application, a percentage by liquid volume (vol %) is calculated based on the volume sum of the constituent elements prior to mixing.

The various steps outlined above are now discussed in turn, including optional and preferred features. Each optional and preferred feature, and combinations thereof, are explicitly disclosed herein with each and every aspect of the invention, to the extent that they are compatible, as if each and every combination was individually and explicitly recited.

Lipid Extraction

Although some methods in the prior art (e.g. protein biotyping) have demonstrated direct analysis from living cells by MALDI-MS, the organic solvent extraction step used in the claimed methods provides several important advantages. These include:
a) Inactivation of the microbe cells, as the cellular structure is destroyed. This facilitates easy handling of the sample (for example, during preparation and in transport), even when working with pathogenic species.
b) Production of a homogenous lipid solution, minimising the effect of the original cell structure on the resultant spectrum. The mass spectra are more reproducible.

c) Ease of storage. Lipids can be stored for a long time (for example, at about −20° C. down to about −80° C.) without showing significant deterioration. In contrast, living cells cannot be stored over the same period. This easy of storage allows analysis to be readily re-run to confirm results.

Generally, any lipid extraction technique can be used that conserves the lipids, preferably at least the phospholipids, intact. This preserves the full biological information content.

In some aspects, the lipid extraction step comprises extraction of lipids from the microbial cells.

In other aspects, the lipid extraction technique comprises extraction of phospholipids from microbial cells. In these aspects, neutral lipids are preferably also extracted.

Typically, the lipid extraction step comprises addition of an organic extraction composition to the microbes. The organic extraction composition preferably comprises one or more organic solvents. In some cases, the organic extraction composition preferably comprises one of more alcohols. The organic extraction composition preferably comprises more than about 50 vol % alcohol, more preferably at least about 51 vol %, 52 vol %, 53 vol %, 54 vol %, 55 vol %, 60 vol %, 70 vol %, 80 vol % or 90 vol %. Short-chain alcohols are preferred, such as $C_{1-4}$ alcohols, with ethanol and methanol particularly favoured because they have been found to effectively extract PLs from all types of microbial cells (i.e. bacteria, yeasts and fungi), independent of the cellular structure. In some cases, the extraction composition comprises up to 100 vol % alcohol, preferably up to 95 vol %, 90 vol %, 85 vol %, 80 vol %, 75 vol % or 70 vol %.

The organic extraction composition may alternatively or additionally comprise ketones, esters, and/or ethers (e.g. MTBE, DIPE), or mixtures thereof.

These solvents are preferred because they are compatible with (i.e. they readily dissolve) the MALDI matrix materials used in the sample preparation step. For this reason, the alcohol based solvents (which comprise at least about 50 vol % alcohol) are particularly favoured. As a result of this compatibility, these solvents generate relatively small background noise signals in the resultant mass spectra. Lipid (and particularly phospholipid) extraction is efficient and reliable, allowing for reproducible spectra to be obtained. Further, no additional reagents are needed, saving cost.

Another preferable feature of the extraction composition is that it is not bi-phasic. In other words, it entirely comprises either polar solvents, or non-polar solvents. No separation step is then necessary, reducing processing time and increasing throughput. In other words, the lipid extraction step simply comprises addition of the solvent to the sample, i.e. it is a single step extraction method. This is in contrast to the Folch reagents, which require the polar and non-polar components to be phase separated after lipid extraction.

In some cases, the extraction composition does not include any halogenated organic solvent. That is, chloroform ($CHCl_3$) is specifically not part of the extraction composition. In other cases, the extraction composition comprises less than 5 vol %, preferably less than 4 vol %, 3 vol %, 2 vol %, 1 vol %, 0.5 vol %, 0.4 vol %, 0.3 vol %, 0.2 vol % or 0.1 vol % of any halogenated organic compounds or solvents (including chloroform).

In some cases, the organic extraction composition preferably comprises or consists of alcohols, as they result in the smallest spectral noise. $C_{1-4}$ alcohols are favoured, and methanol is particularly preferred. The organic solvent may substantially consist of methanol.

In other cases, the organic extraction composition preferably comprises or consists of an alcohol/ketone mixture, preferably in a ratio by volume of from about 70:30 or 75:25 to about 85:15 or 90:10. In preferred cases, the organic extraction composition comprises a $C_{1-4}$ alcohol and a $C_{3-4}$ ketone mixture, in that ratio range. In particularly preferred cases, the organic extraction composition comprises of a methanol/acetone mixture, in that ratio range. Most preferably, the organic extraction composition consists of a methanol/acetone mixture in a ratio by volume of from about 70:30 or 75:25 to about 85:15 or 90:10. These mixtures are particularly preferred because they effectively extract a diverse range of lipid classes which have different polarities (including cationic and anionic phospholipids, and neutral lipids), whilst minimising spectral noise and allowing reproducible spectra to be obtained.

Alternatively, the organic extraction composition comprises more than 50 vol % ether, preferably at least about 55 vol %, 60 vol %, 70 vol %, 80 vol % or 90vol %. $C_{1-4}$ ethers are preferred (by which we mean, the carbon chain on either side of the ether linkage contains a between 1 and 4 carbons). Preferably the ether volume comprises or consists of diisopropylether (DIPE). The ether-based organic extraction composition may additionally comprise alcohols, ketones and/or esters, or mixtures thereof.

As discussed below, where the method includes protein extraction, the extraction step may include the use of water, either as part of the extraction composition or as a precursor step in which water is added to the microbes.

Preferably, the extracted sample is treated to remove contaminants such as proteins. This improves the reproducibility and clarity of the resultant spectra. Naturally, where the method includes extraction and analysis of proteins, this optional contaminant removal treatment is either not carried out or is adjusted so as to preserve (or at least minimise removal of) proteins.

In the case of protein contaminants (at least), these are preferably precipitated out of the extracted solution and removed by centrifugation.

Protein extraction

The present inventors have found that, surprisingly, the extraction methods and solvent systems discussed herein in respect of lipid extraction are also effective to extract proteins from the microbes and to permit the extracted proteins to be analysed by MALDI mass spectrometry.

Furthermore, the present inventors have established that use of protein m/z data in combination with lipid m/z data can provide increased accuracy and confidence in the resultant species and, in particular, sub-species identification.

The present inventors have found that the use of water, in addition to the alcohol/ether components of the extraction composition, can assist in facilitating the availability of proteins for subsequent MALDI-MS analysis. This can be achieved by combining/mixing water with the microbe (e.g. with the cell culture). This can be done in a first/precursor step before combining/mixing with the alcohol/ether components and/or by including water in the alcohol/ether extraction composition.

The present inventors have found that use of water assists in preparing a suspension (of the microbe material) which facilitates formation of a good quality MALDI sample. Thus, swelling and/or spreading out and/or dispersion of the microbes (e.g. cells from a culture) can be assisted by the use of water, especially in a first/precursor step prior to combining/mixing with alcohol/ether.

Typically, after the step of combining/mixing with water and/or the extraction composition, the resultant material is sonicated. Typically (ultra)sonication is carried out for at least 1 minute, suitably at least 2 minutes, preferably at least 5 minutes. Typically, sonication is carried out for no more than about 20 minutes, typically no more than 15 minutes. A particularly preferred range is 5 to 10 minutes.

Optionally, the composition comprising the extracted lipids and/or proteins can be cooled, for example to <20° C., for example to <10° C., for example to <5° C. This can conveniently be achieved by placing the sample (in a suitable container/vessel) on/in ice. The present inventors have found that this can further enhance the quality of the extract for subsequent MALDI-MS analysis. The duration of any such cooling step is typically at least 10 minutes, suitably at least 20 minutes, and preferably at least 25 minutes. Generally, the cooling step is no longer than 60 minutes, typically no more than 45 minutes, and preferably no more than 35 minutes. In embodiments, cooling is for about 30 minutes.

The composition comprising extracted lipids and/or proteins can optionally be vortexed. Generally this is done in combination with, suitably after, cooling as discussed above. Again, this has been found to further improve the homogeneity of the suspension formed from the addition of the extraction composition to the microbes, which in turn improves the quality of the MALDI-MS spectra.

The use of water as well as alcohol/ether in this way, suitably with ultrasonication, facilitates production of a homogenous suspension of hydrophilic and hydrophobic components (including cellular proteins and membrane lipids). This permits effective analysis, from the same sample, of both proteins and lipids using MALDI-MS.

Sample Preparation

The sample preparation step comprises addition of the extracted lipids to a matrix material. In embodiments where protein analysis is carried out, the sample preparation step comprises addition of the extracted proteins to a matrix material. As discussed below, the matrix material used for lipid analysis can be different to the matrix material used for protein analysis.

The matrix used in MALDI-MS acts a) as an ionization promoter of the lipid molecules and b) as an ionisation moderator to prevent fragmentation of the relatively labile lipid molecules. The matrix selected is not particularly limited, provided that this function is realised. 2,5-dihydroxybenzoic acid (2,5-DHB), 2,4-dihydroxybenzoic acid (2,4-DHB), 6-aza-2-thiotymine (ATT), 9-aminoacridine (9AA) and 2,4,6-trihydroxyacetophenone (THAP) are all suitable matrix materials. That is, in some cases the matrix material comprises one or more of these compounds.

The matrix used may depend on whether the mass spectrometer is operated in the positive or negative mode. That is, whether the lipids will be positively or negative ionised.

Some example matrix materials are discussed below, which are particularly preferred when working with phospholipids (and neutral lipids where they are also extracted).

For a system operating in the positive mode, a 2,4,6-trihydroxyacetophenone (THAP) matrix is preferred. It is particularly preferred when doped with sodium or lithium acetate (ionisation promoters), which allow for detection of neutral lipids by formation of positively charged sodium adduct ions (See FIG. 3). The concentration range of the salt doping is preferably about 1-50 mM, preferably 10-20 mM. Doping at these levels allows complete suppression of other unwanted alkali counter ions within the MALDI mass spectra.

6-aza-2-thiotymine (ATT) is a preferred matrix material when operating in the positive mode. This is particularly good for the detection of cationic PLs. ATT results in a softer ionization than THAP, and leads to less pronounced generation of fragmentation products, and so the resultant spectra are easier to analyse. It is particularly preferred when doped with di-ammonium hydrogen citrate (DAHC), which suppresses the formation of mixed alkali adducts (e.g. Na or K) and allows for detection of exclusively protonated PLs (See FIG. 3). The concentration range of the salt doping is preferably about 1-100 mM, more preferably 10-50 mM. Doping at these levels allows exclusive detection of protonated molecular ions within the MALDI mass spectra.

Note that ATT is preferred to THAP, because ATT can be used with ionising lasers which have a greater range of wavelengths (i.e. ATT is compatible with a greater range of lasers).

9-aminoacridine (9AA) is a preferred matrix material when operating in the negative mode. This is particularly good for the detection of anionic PLs. In particular, 9AA doped with guanidine-HCl (9AA-GUA) or doped with pyridine (9AA-PYR) are particularly preferred, because the sensitivity of detection is increased and clear, reproducible spectra result (See FIG. 3). The 9AA-GUA preferably comprises from about 3 mM or 4 mM to about 6 mM or 7 mM of guanidine, most preferably about 5 mM. The 9AA-PYR preferably comprises about 0.3 vol % or 0.4 vol % to about 0.6 vol % or 0.7 vol % of pyridine, most preferably about 0.5 vol %.

In the above systems, the dopants (DAHC, GUA, PYR) each modulate the contribution of alkali salt adducts in the resultant mass spectra, and promote the detection of $[M+H]^+$ and $[M-H]^-$ ions in the positive and negative modes respectively.

In some cases, a solution of the extracted lipids is added to a solution of the matrix material. In such cases, the lipid solution preferably has a lipid concentration of from about 0.5 or 1 to about 10 or 20 µM, to provide the best mass spectral quality and reproducibility.

In other cases, the matrix material solution is added to the microbial sample directly. The solvent used to dissolve the matrix material extracts lipids from the microbial sample, which then form a MALDI sample with the matrix material. This technique allows so called "on-target" lipid extraction; that is, lipid extraction on a MALDI sample plate. This is a faster processing technique and thus allows a higher analysis throughput.

In either case, the molar ratio of matrix material to lipids is suitably from about 50000:1 to about 2500:1.

In respect of embodiments where proteins are extracted and analysed, the MALDI matrix material is suitably selected from α-Cyano-4-hydroxycinnamic acid (CHCA), sinapinic acid (SA) and ferulic acid (FA). CHCA is preferred.

The MALDI sample is preferably from about 0.5 µL to about 1.5 µL in volume, most preferably about 1 µL.

Preferably, the sample is prepared on a polymeric or plastics MALDI sample plate, rather than a conventional steel target. This minimises background noise especially in the low mass range (i.e. m/z<1000) where the majority of lipids are detected. For example, 48-well FlexiMass™-DS (Shimadzu) target slides can be used.

Data Gathering

Data can be gathered with a mass spectrometer operating in the positive mode (positive ionisation of the sample) and/or the negative mode (negative ionisation of the sample).

The presence of both cationic and anionic phospholipid species within microbes means that the use of both modes is necessary to assess all lipids in the cell membrane. However, the inventors have found that single mode data gathering is sufficient to obtain reliable results and to provide a lipid fingerprint which allows microbial identification.

The negative mode is preferred for the following reasons:
(a) Anionic PLs are prevalent in the cell membrane of most bacteria and other microbes. More signals are present in the resultant spectra, thereby allowing for easier analysis and microbial identification.
(b) Fatty acids (FAs) can be detected in the negative mode, which considerably increases the spectral information content and aids in microbial identification. These are detected as carboxylate anions.
   FAs are important structural components of lipids and have already been used for chemotaxonomic purposes.[16] The extra information content assists in differentiation of microbial strains.
(c) The noise from contaminants is typically lower. In particular, the inventors found that contaminants from typical culture medium (such as blood agar) contain cationic PLs, which are detected in the positive mode, but not in the negative mode.

The m/z range scanned is preferably from about 100 to about 3000. This wide range allows detection of both intact lipids (typically m/z >500) and fatty acid residues (m/z typically <500). Thus, the method may be characterised in that the m/z range includes the range <500, for example about 100 to <500. More preferred m/z ranges may be from about 200, 300, 400 or 450 to about 1500, 1800, 2000, 2500 or 2800. In embodiments, the m/z range includes the range from about 100 to about 500, suitably about 100 to <500, preferably about 100 to about 450, more preferably about 100 to about 400.

In prior art methods, the lower end of this range (m/z <500) is not typically scanned due to high noise levels. However, the present inventors have found that detection of fatty acid may improve the information content of the spectra.

As discussed herein, in embodiments where protein is extracted and analysed, the data gathering step of the method includes scanning the m/z range for protein information, typically from about 2000 to 20000. Typically this is done as a separate step, i.e. a MALDI-MS experiment, such that in embodiments the data gathering step comprises two stages—one for scanning the m/z range for lipids (and preferably also fatty acids), and one for scanning the m/z range for proteins.

By obtaining both protein and lipid composition information (fingerprint) from the same microbes, facilitated by the sample preparation techniques discussed herein, more data is available for identification of the microbe (species and sub-species). This can provide more accurate microbe identification, with higher level of confidence in the result.

The mass spectrum data for the lipids and the mass spectrum data for the proteins can be combined/merged. This can be achieved by exporting the protein and lipid data sets to a spreadsheet such as Micorsoft Excel and merging them. Cluster and/or other analysis can then be carried out as discussed herein.

To minimise background noise in the low mass range (i.e. m/z<1000), a polymeric or plastics MALDI sample plate (rather than a conventional metal target) is used in preferred cases.

Lipid peaks in mass spectra are detected in a similar mass range to background signals. Thus, high resolution instruments and techniques are preferably used.

As such, one or more of the following mass spectrometry techniques may be used during the data gathering step:
a) Quadrupole ion trapping (QIT).
b) Time of flight measurement (TOF).
c) Reflection time of flight measurement (RTOF).
d) Orbitrap mass spectrometry.
e) Fourier transform mass spectrometry (FTMS).
f) Tandem mass spectrometry (MS/MS).

Low- or high- energy collision induced dissociation (CID) can also be used to improve the FA information content.

Generally, these techniques improve the reproducibility of the spectra, which is very important to achieve reliable microbial identification. They may also increase the number of data points recorded.

These techniques are relatively simple to use and contribute to one or more of the following advantages;
increased mass accuracy;
increased mass spectral resolution;
reduced mass spectral noise;
increased information content.

Most preferably QIT-TOF, multistage tandem mass spectrometry (MSn) is used.

MSn also allows both lipid profiling in the MS1 mode and structural elucidation of the individual lipid species mainly in the MS2 or MS3 modes.

Microbe Identification

In this step, the data gathered is analysed to identify or characterise the microbial strain.

The may comprise comparison of the data with existing data libraries. These libraries may contain lipid mass fingerprints and/or protein mass fingerprints for microbial strains.

In some cases, the microbe strain is definitively identified.

In other cases, the microbe can be characterised based on its lipid profile and preferably also its protein profile. Certain properties, such as susceptibility to antibiotics and pathogenicity can be predicted or determined.

Microbe Cultivation

The microbes may be cultivated prior to lipid extraction.

Microbial lipid compositions are known to change over time. In aspects where the microbe is identified or characterised, it is preferred that the cultivation step follows a fixed procedure.

In some cases, microbial strains may be cultivated in liquid or on solid culture media. Alternatively, they may be cultivated using blood agar or minimal medium (e.g. LB Agar). Blood agar is a preferred medium for bacterial cell culture, because it contains all necessary nutrients and bacterial growth is faster. In this case, the use of the negative ionisation mode is preferred, to minimise noise signals originating from the culture medium.

In some cases, yeast strains may be grown on a GYP (glucose, yeast extract, peptone) medium.

In some cases, filamentous fungi may be grown on a Malt extract agar.

The cultivation period and environmental conditions are preferably the same in the sample cultivation as those used in the obtaining of any comparative data.

The cultivation may last for a fixed period of time. This may be 12 hours, 24 hours, 36 hours, 48 hours, 72 hours or longer. The precise length of time is not particularly important.

The, environmental conditions during cultivation are preferably as follows; from about 15° C. or 20° C. to about 25° C. or 37° C. The cultivation preferably takes place in air.

DETAILED DESCRIPTION

Features of the invention will now be described in detail with reference to the accompanying figures, in which:

FIG. 1 compares the relative lipid extraction efficiency of 6 different organic solvents (NL=neutral lipids; PL=phospholipids).

Figure 4:
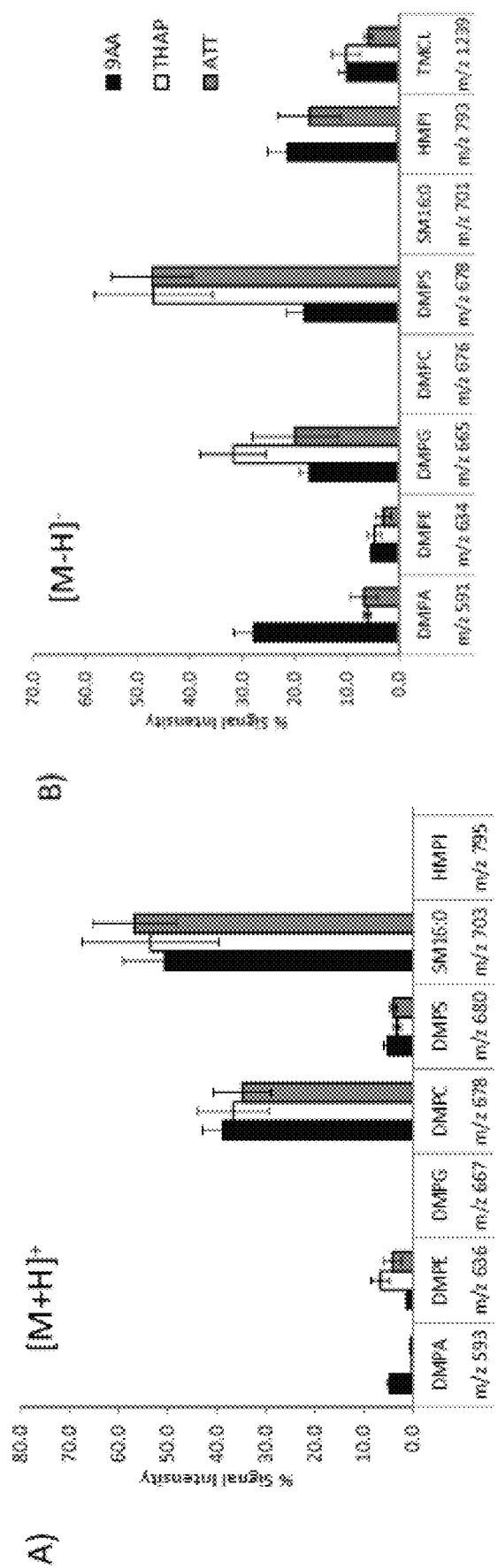

FIG. 4 compares the relative signal strengths resulting from various lipid classes in (A) positive ionisation mode and (B) negative ionisation mode, and using three different matrix substances.

Figure 5:
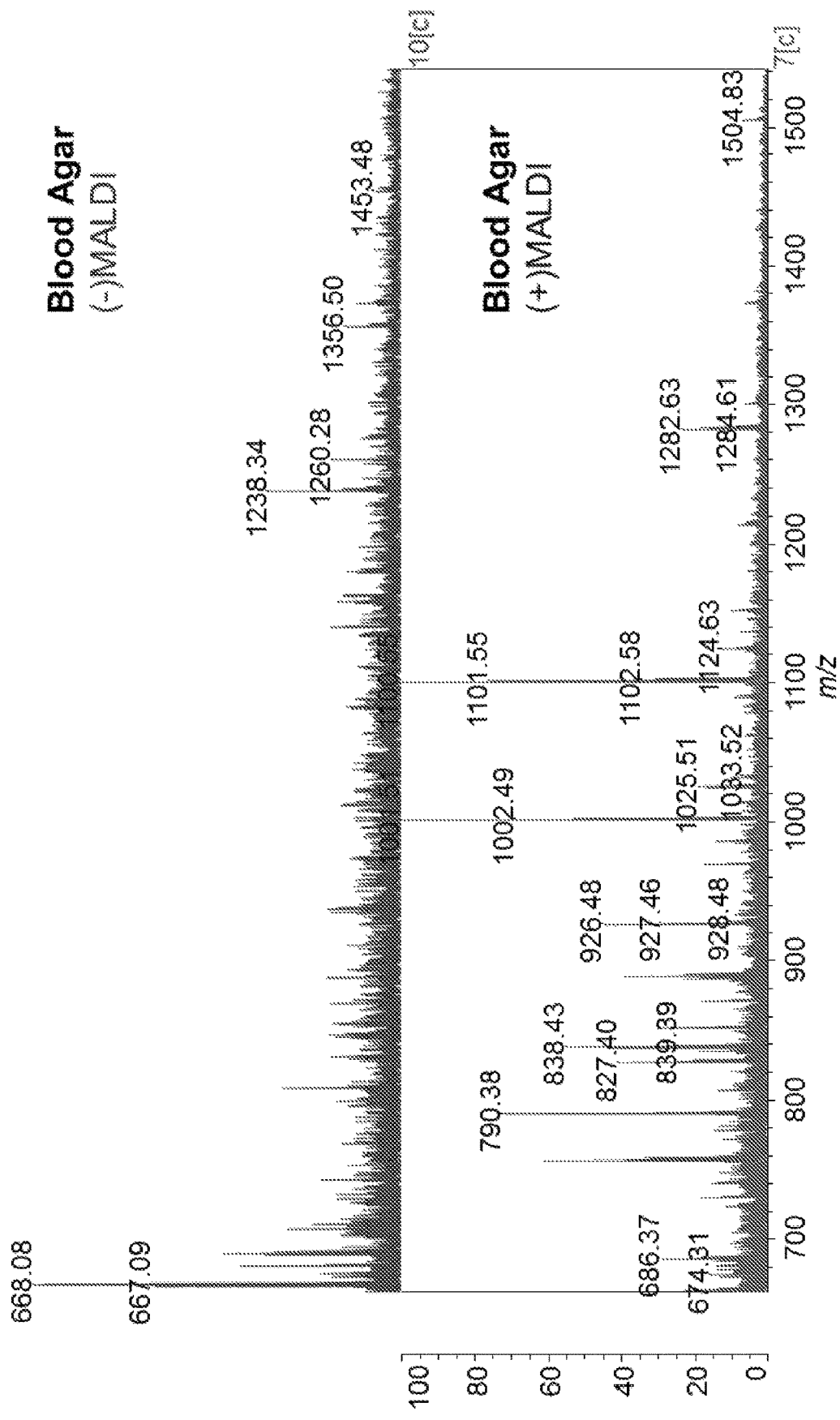

FIG. 5 shows two lipid MALDI-MS spectra obtained from blood agar, one obtained in the positive ionisation mode (bottom trace), and one in the negative ionisation mode (top trace).

Figure 6A:
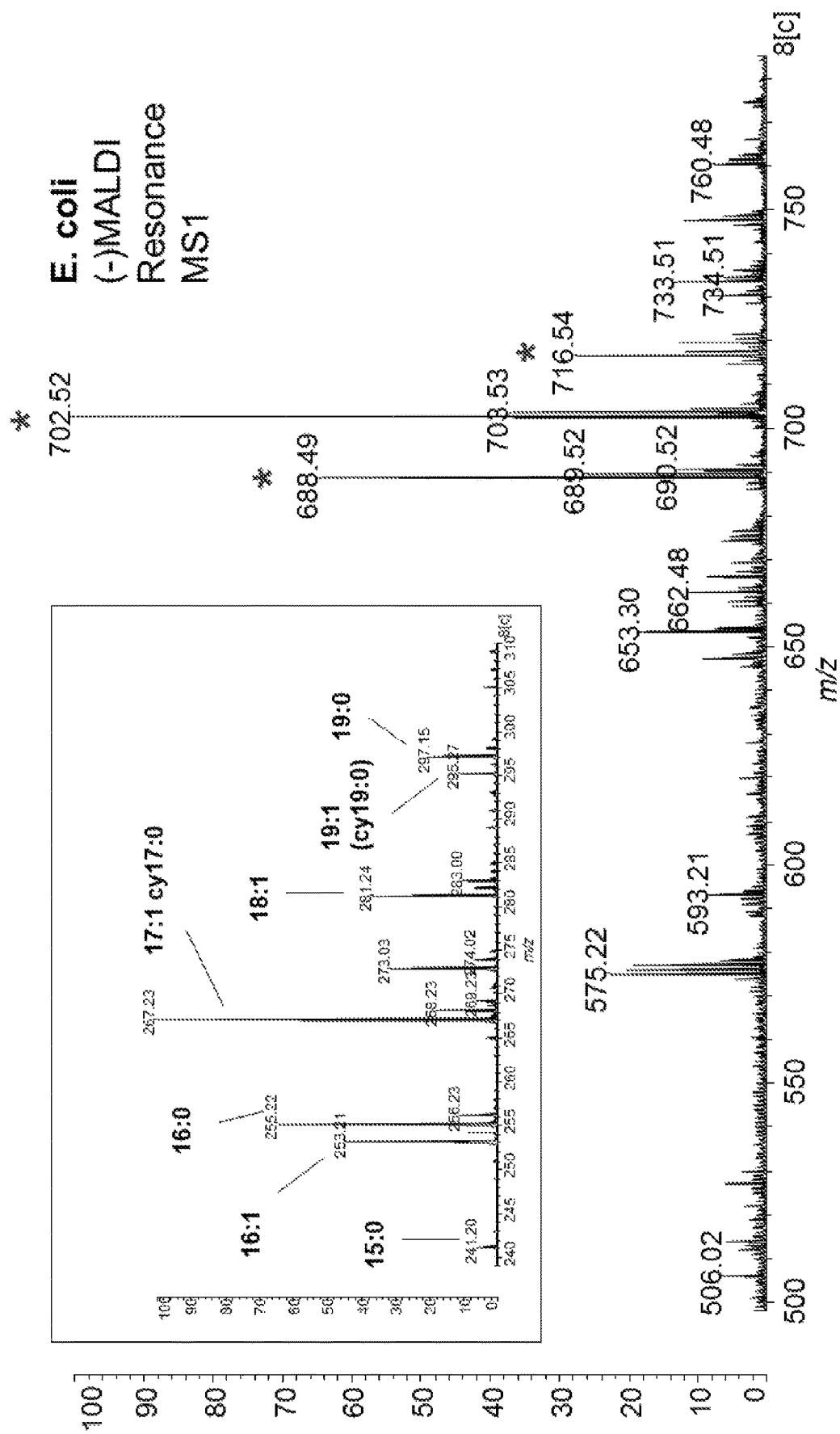

FIG. 6A shows a lipid MALDI-MS spectrum obtained on an *E. coli* strain detected in the negative ionisation mode. This is the MS1 spectrum in the range m/z 500-800 displaying data representative of intact PLs. The inset shows the same spectrum in the range m/z 240-310 displaying data representative of FA fragment ions.

Figure 6B:
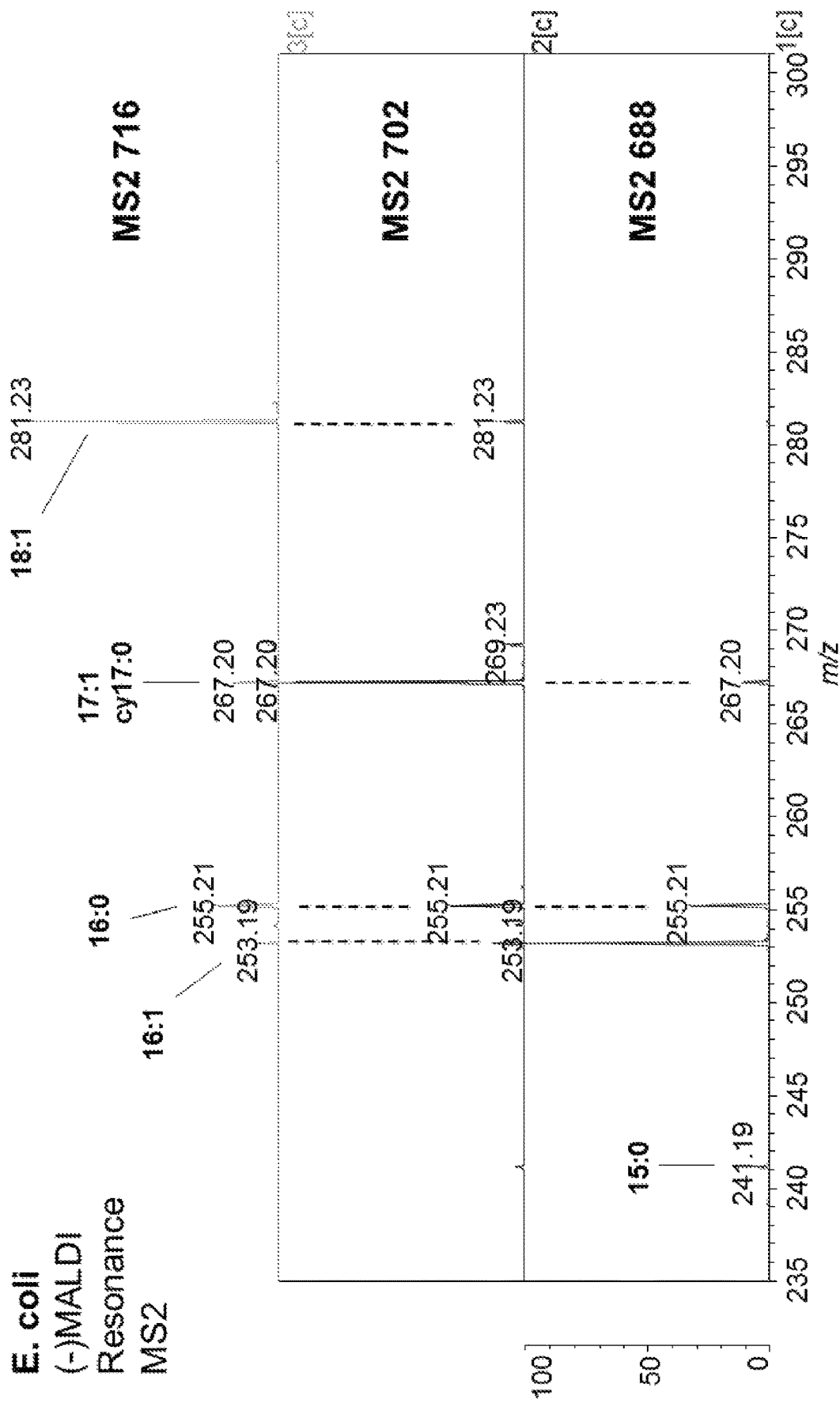

FIG. 6B shows the MALDI-MS/MS spectra of the three major lipid species at m/z 688, 702, and 716 of the same *E. coli* strain as used in FIG. 6A. The data was obtained by tandem mass spectrometry. These are MS2 spectra, and allow the individual lipids to be identified.

Figure 7A:
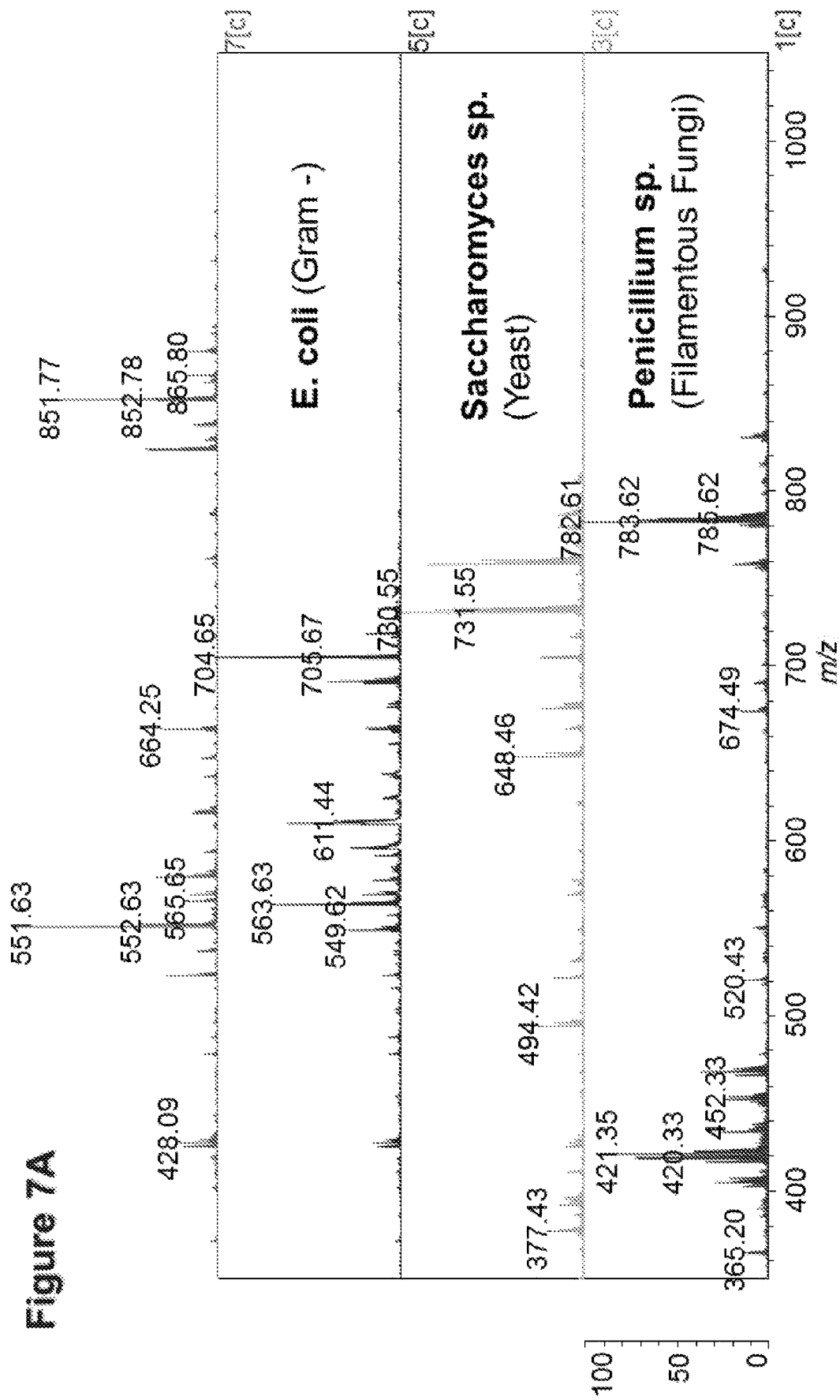

FIG. 7A shows lipid MALDI-MS spectra obtained in the positive mode for 4 different microbes (top trace=*S. aureus*, second trace=*E. coil*, third trace=*Saccharomyces* sp. (yeast), bottom trace=*Penicillium* sp. (filamentous fungi)).

Figure 7B:
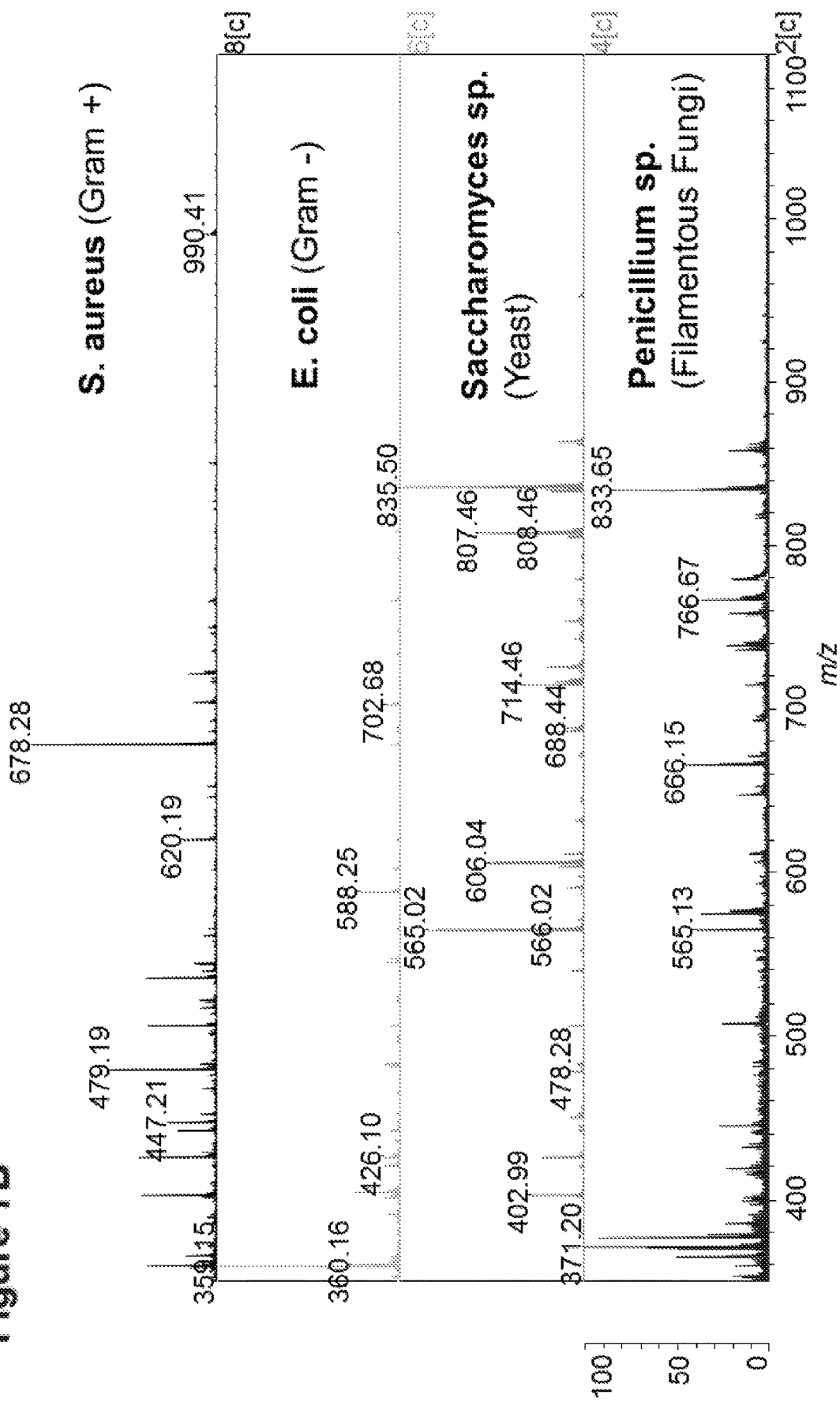

FIG. 7B shows lipid MALDI-MS spectra obtained in the negative mode for the same 4 different microbes (trace order is the same as FIG. 7A).

Figure 8A:
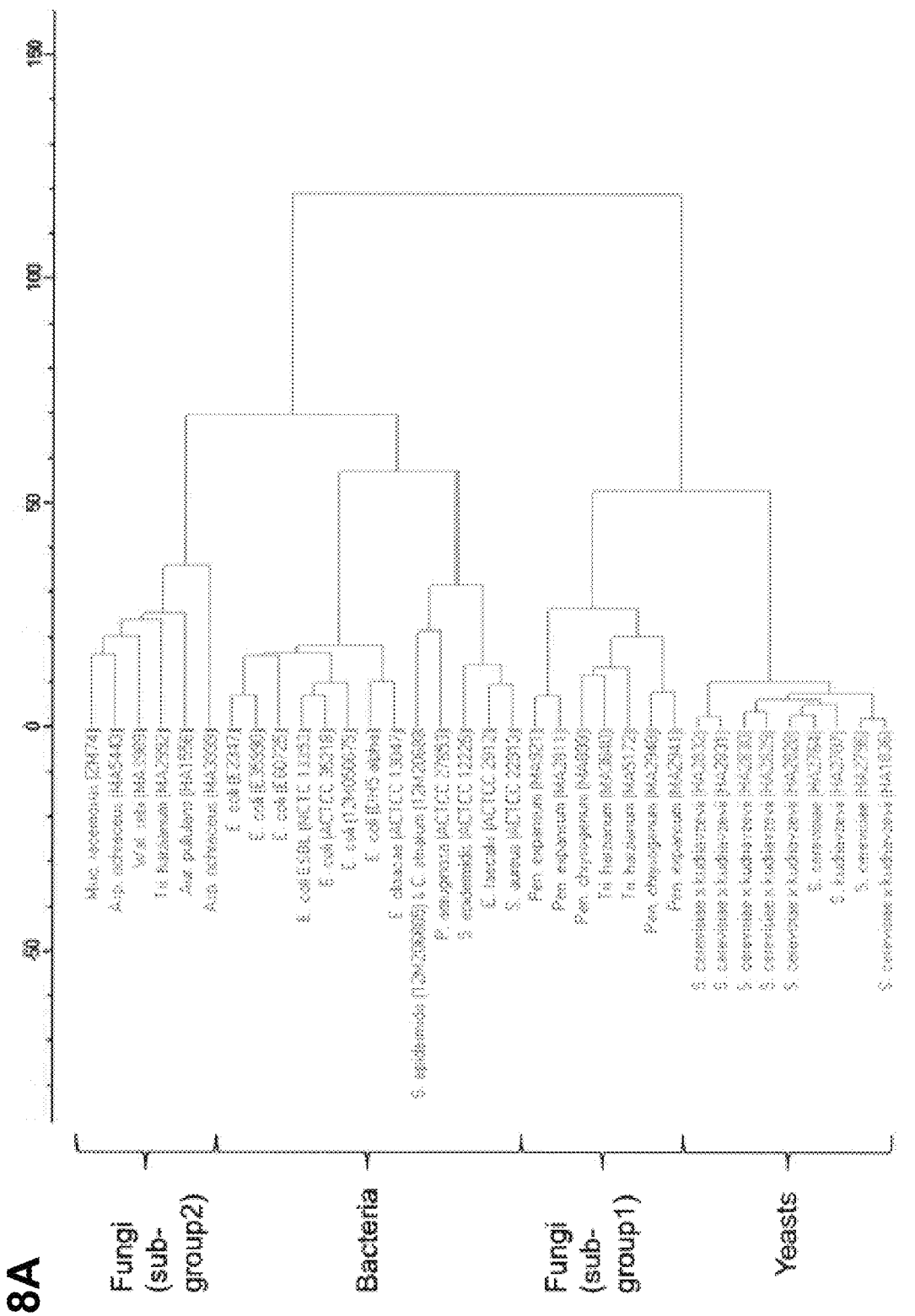

FIG. 8A shows a cluster analysis based on positive mode MALDI-MS data for all of the microbes listed in table 1.

Figure 8B:
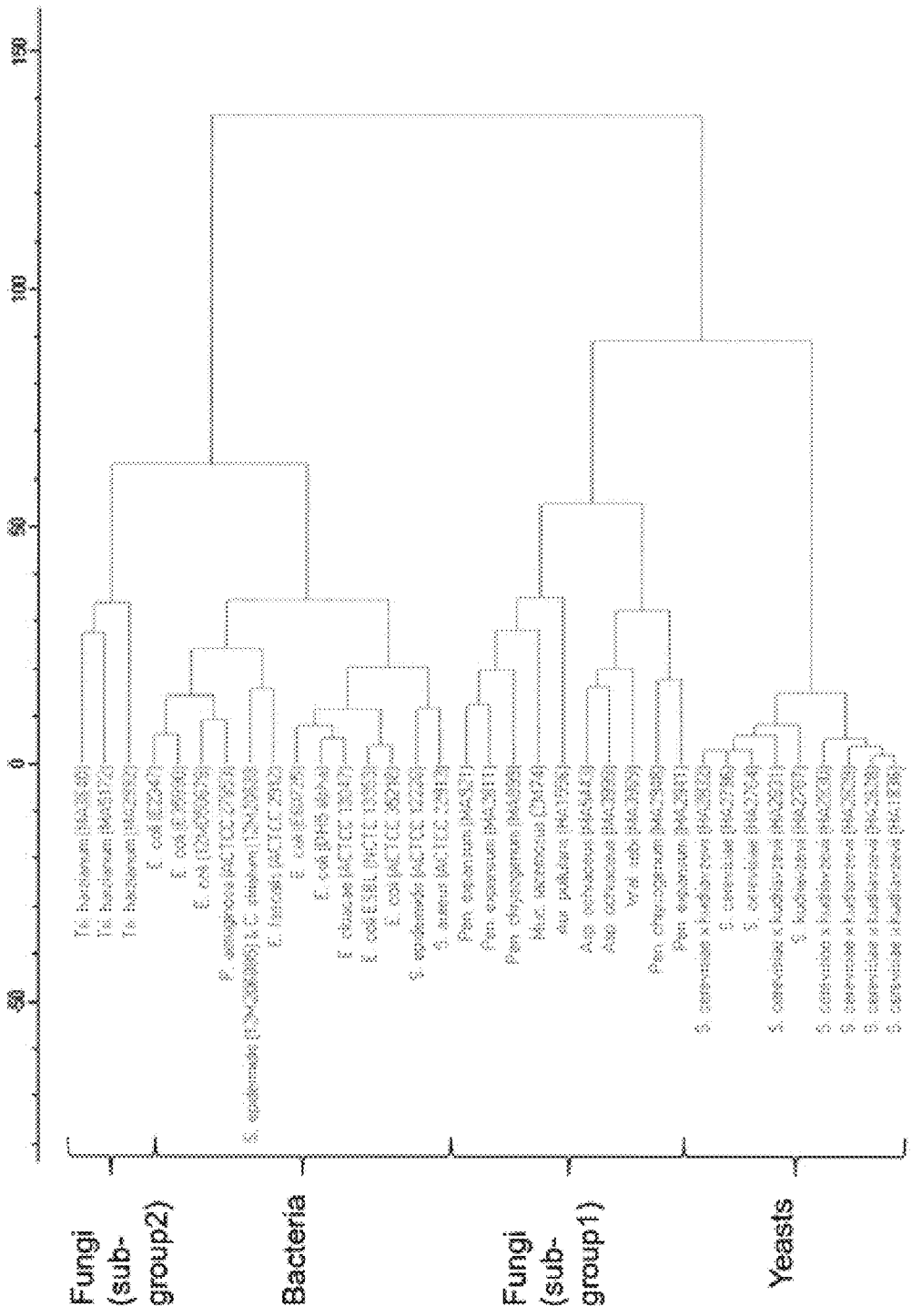

FIG. 8B shows a cluster analysis based on negative mode MALDI-MS data for all of the microbes listed in table 1.

Figure 9:
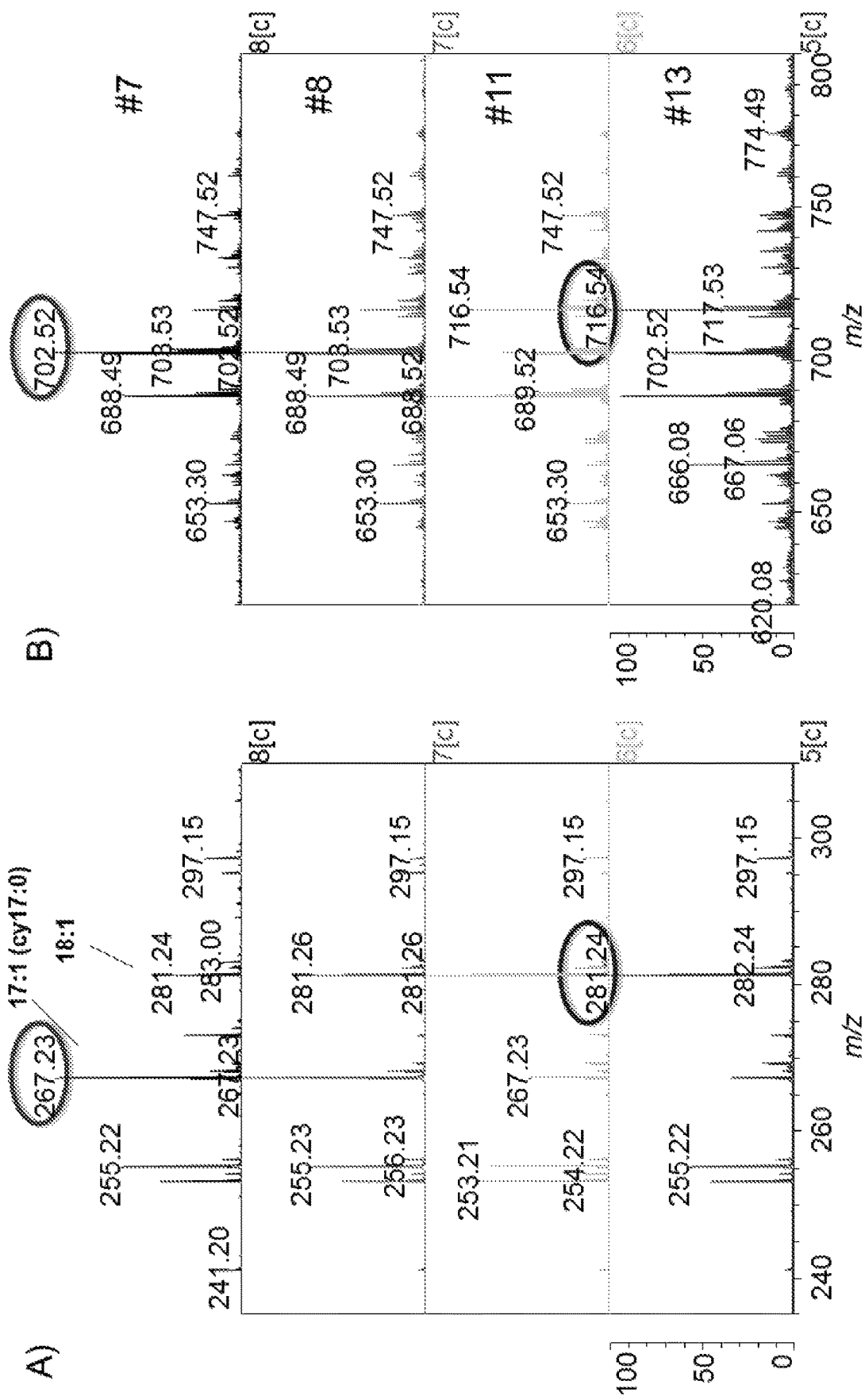

FIG. 9 shows negative mode MALDI mass spectra displayed in (A) the m/z range 240-310 and (B) 650-800 of four *E. coli* strains from Table 1.

Figure 10:
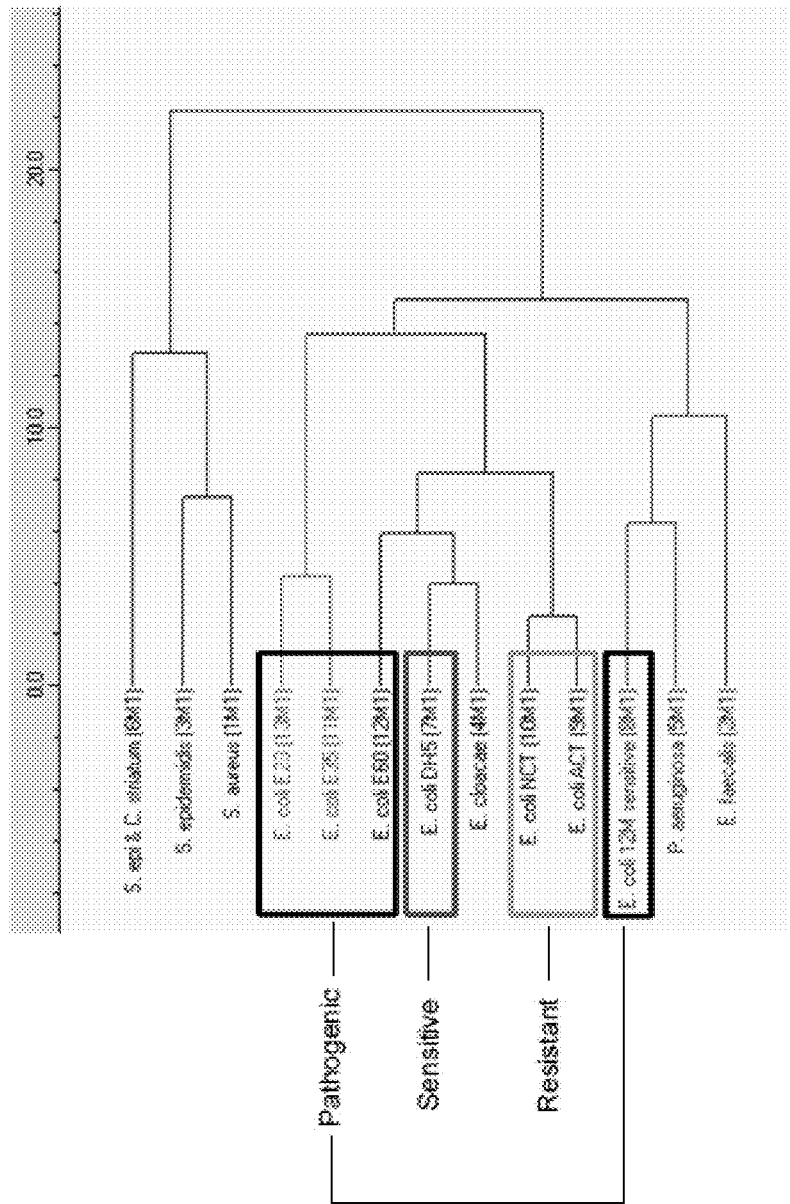

FIG. 10 shows a cluster analysis based on negative mode MALDI-MS data for the bacterial strains listed in Table 1.

Figure 11:
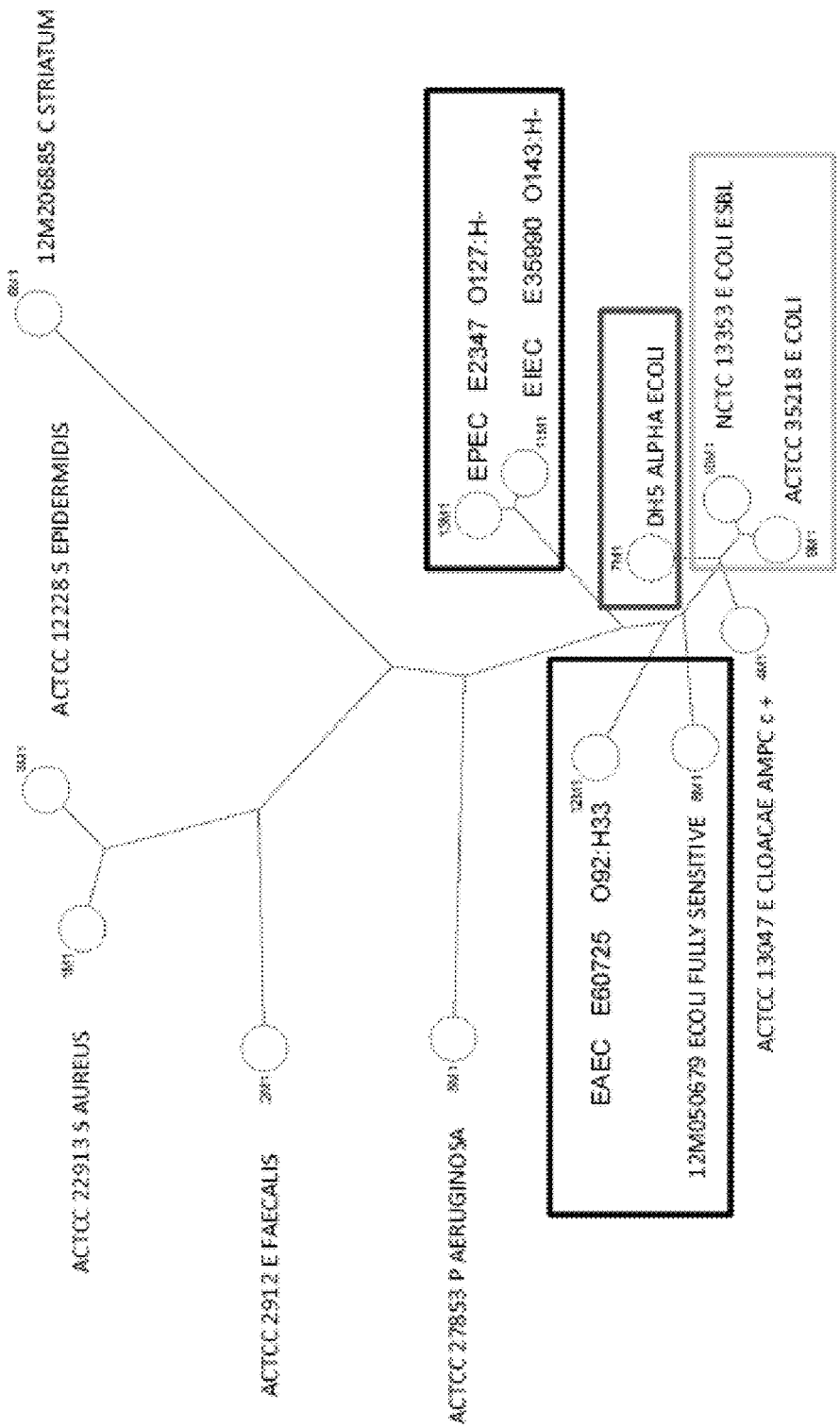

FIG. 11 shows a minimal spanning tree (MST) illustrating the relative relatedness of the bacterial strains listed in Table 1.

Figure 12A:
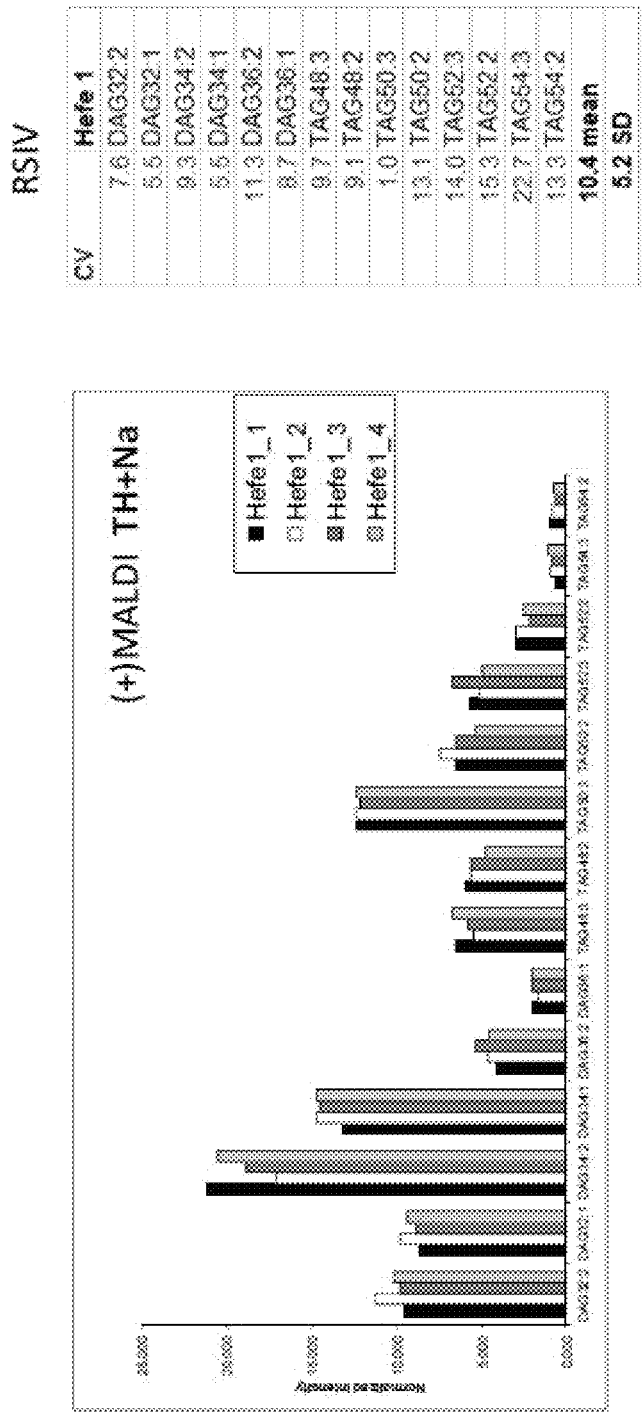
Figure 12B:
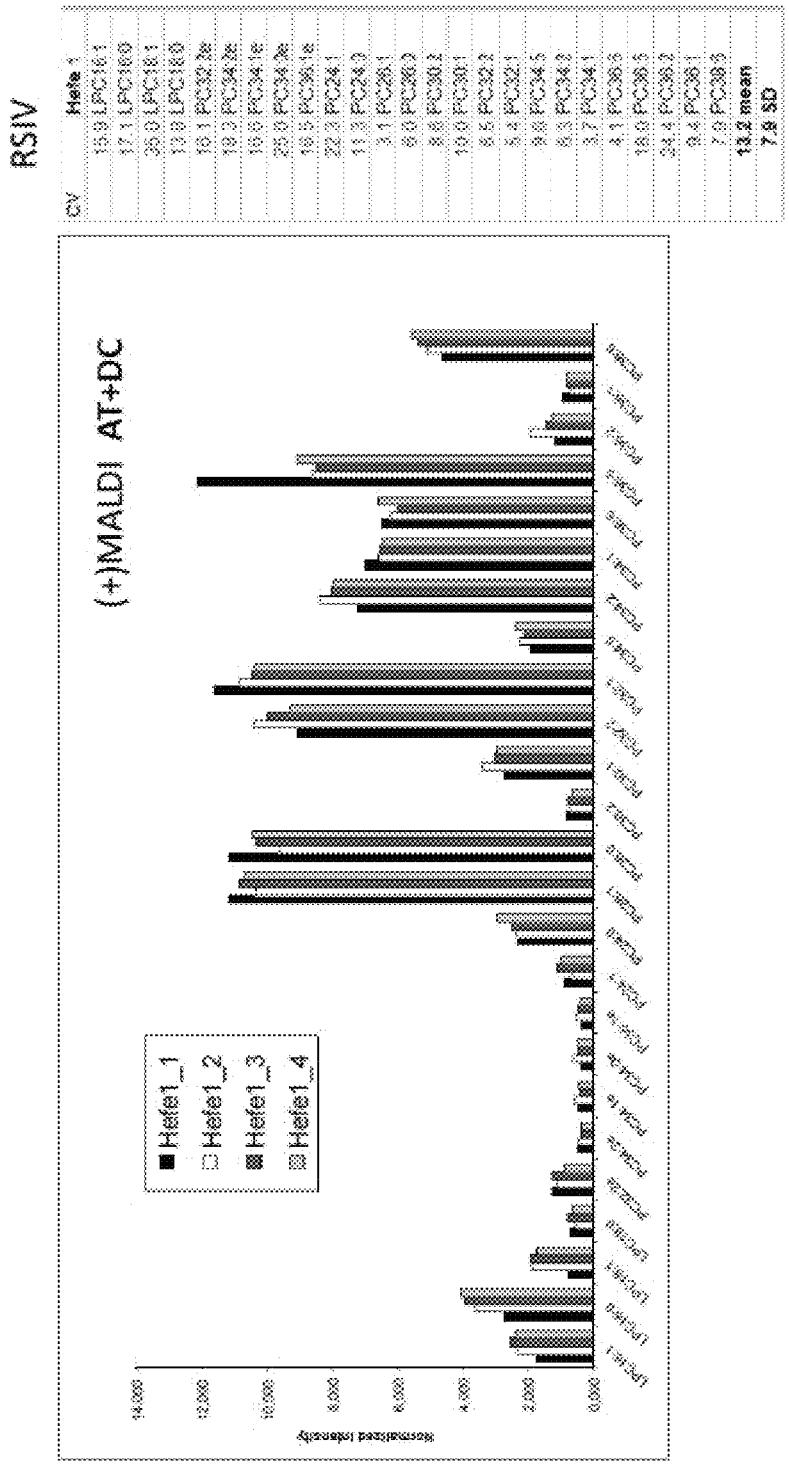

FIGS. 12A to C show the lipid profiles of four independent MALDI-MS measurements of A) NLs detected in the positive mode, B) cationic PLs detected in positive mode and C) anionic PLs detected in negative mode, respectively.

Figure 13:
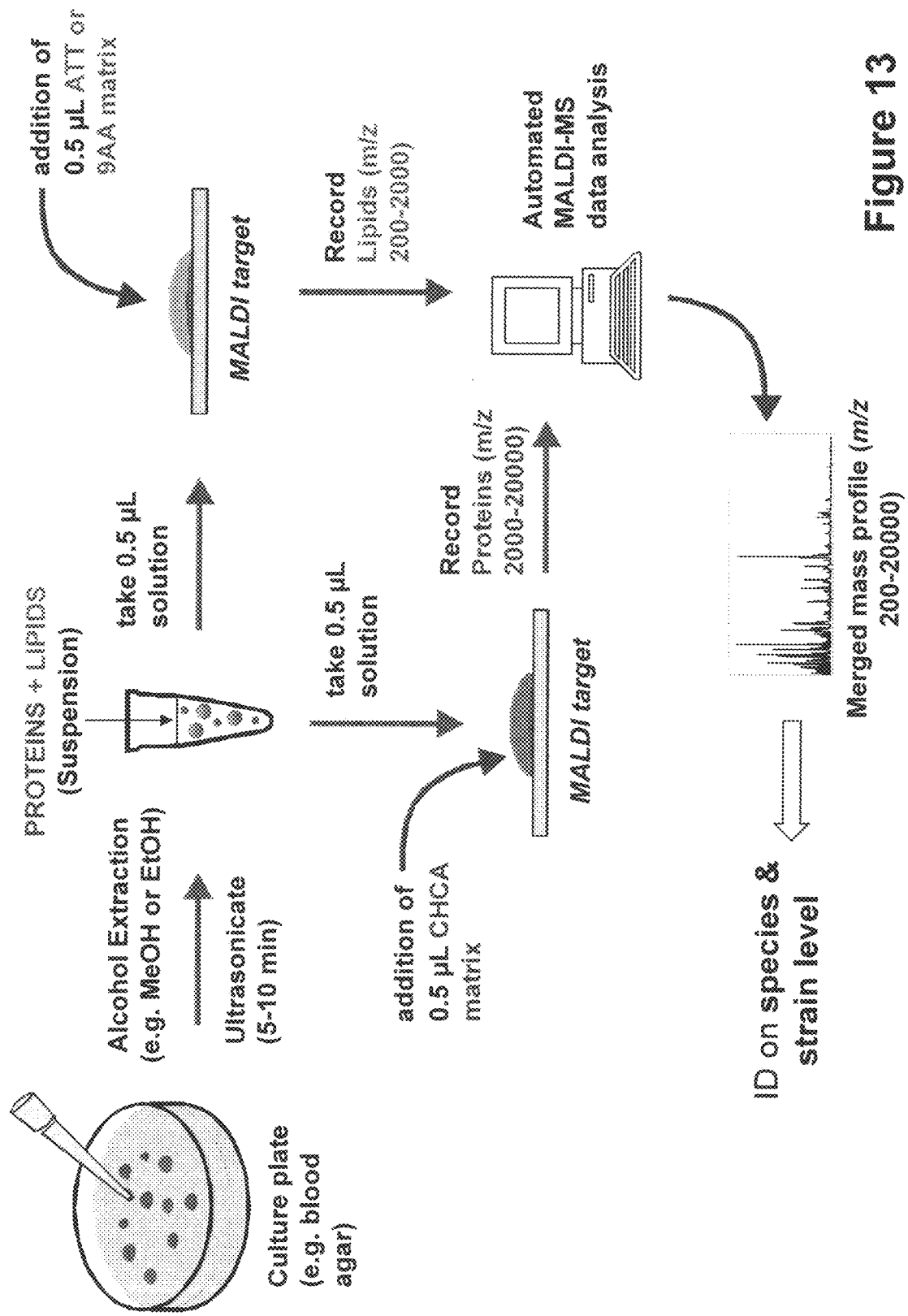

FIG. 13 is a schematic of an "all in one" microbe identification approach comprising preparation, from the same microbes (cell culture), of a MALDI sample for lipid analysis and a MALDI sample for protein analysis, and subsequent MALDI-MS measurements on both samples.

Figure 14A:
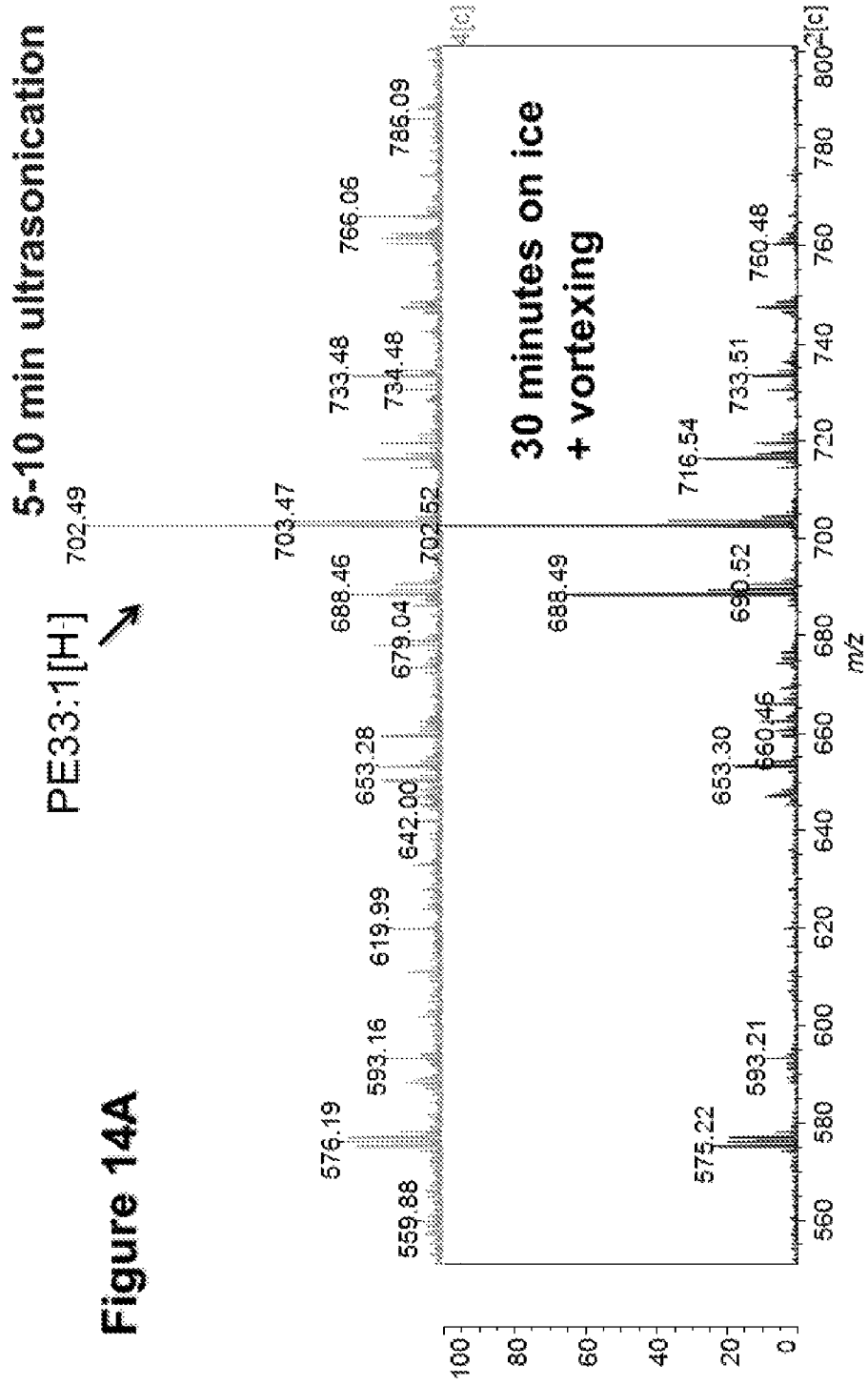

FIG. 14A shows a (−)MALDI −MS spectra of Gram(−) *E. coli* DH5D: 9AA matrix (upper trace after 5-10 minutes ultrasonication; lower trace after cooling and vortexing).

Figure 14B:
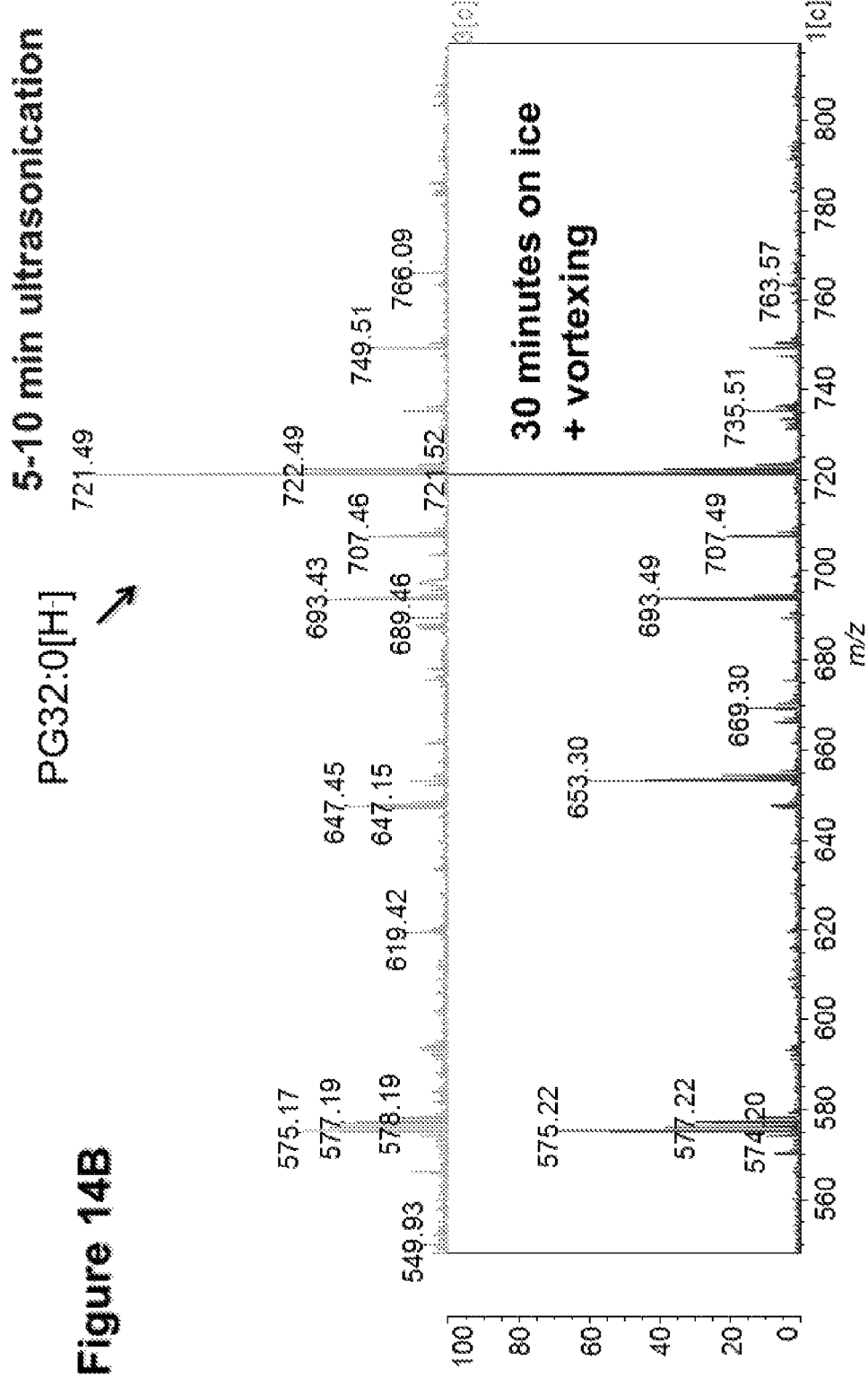

FIG. 14B shows (−)MALDI −MS spectra of Gram (+) *S. aureus:* 9AA matrix (upper trace after 5-10 minutes ultrasonication; lower trace after cooling and vortexing).

Figure 14C:
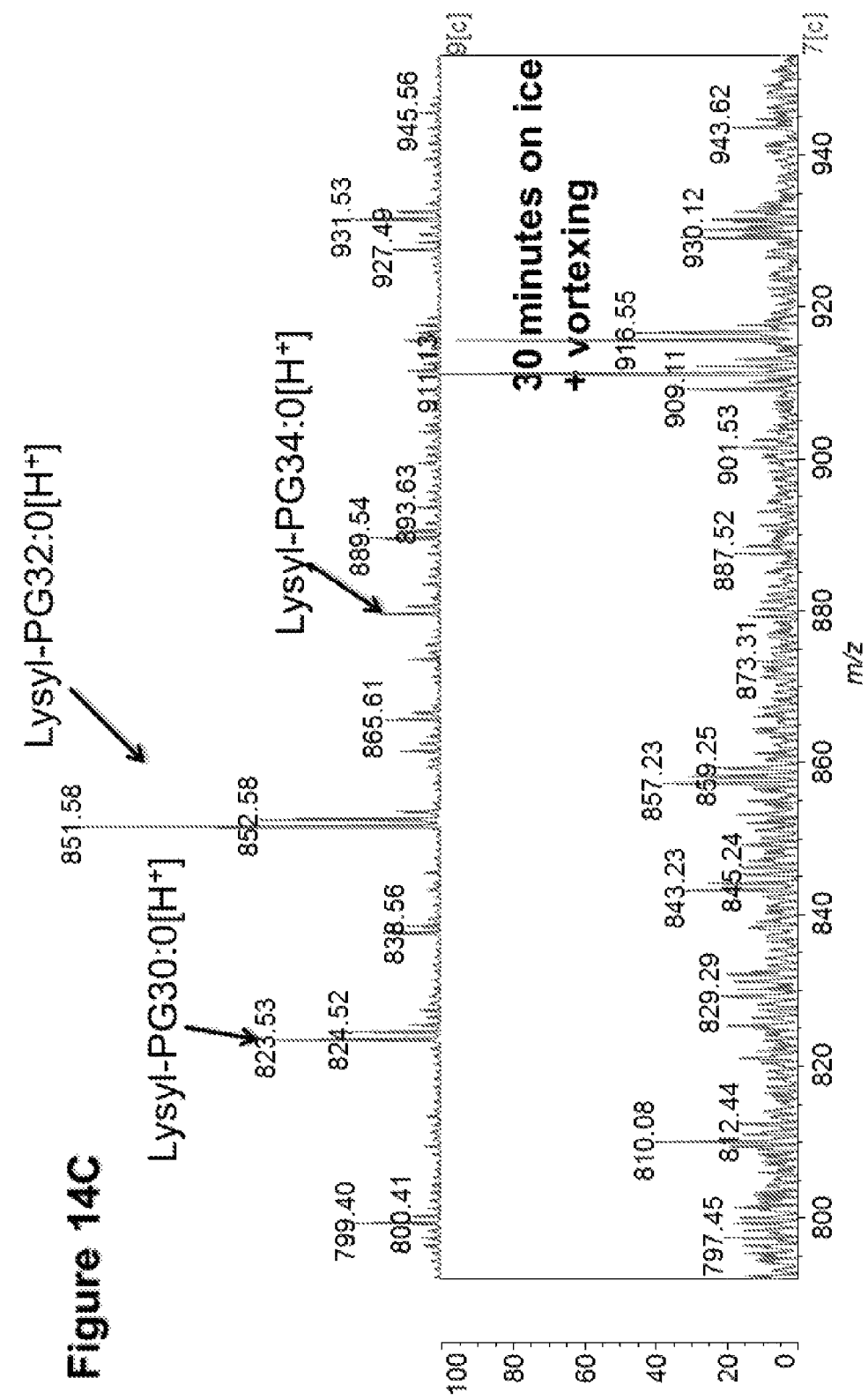

FIG. 14C shows (+)MALDI −MS spectra of *S. aureus:* ATT matrix (upper trace after 5-10 minutes ultrasonication; lower trace after cooling and vortexing).

Figure 15:
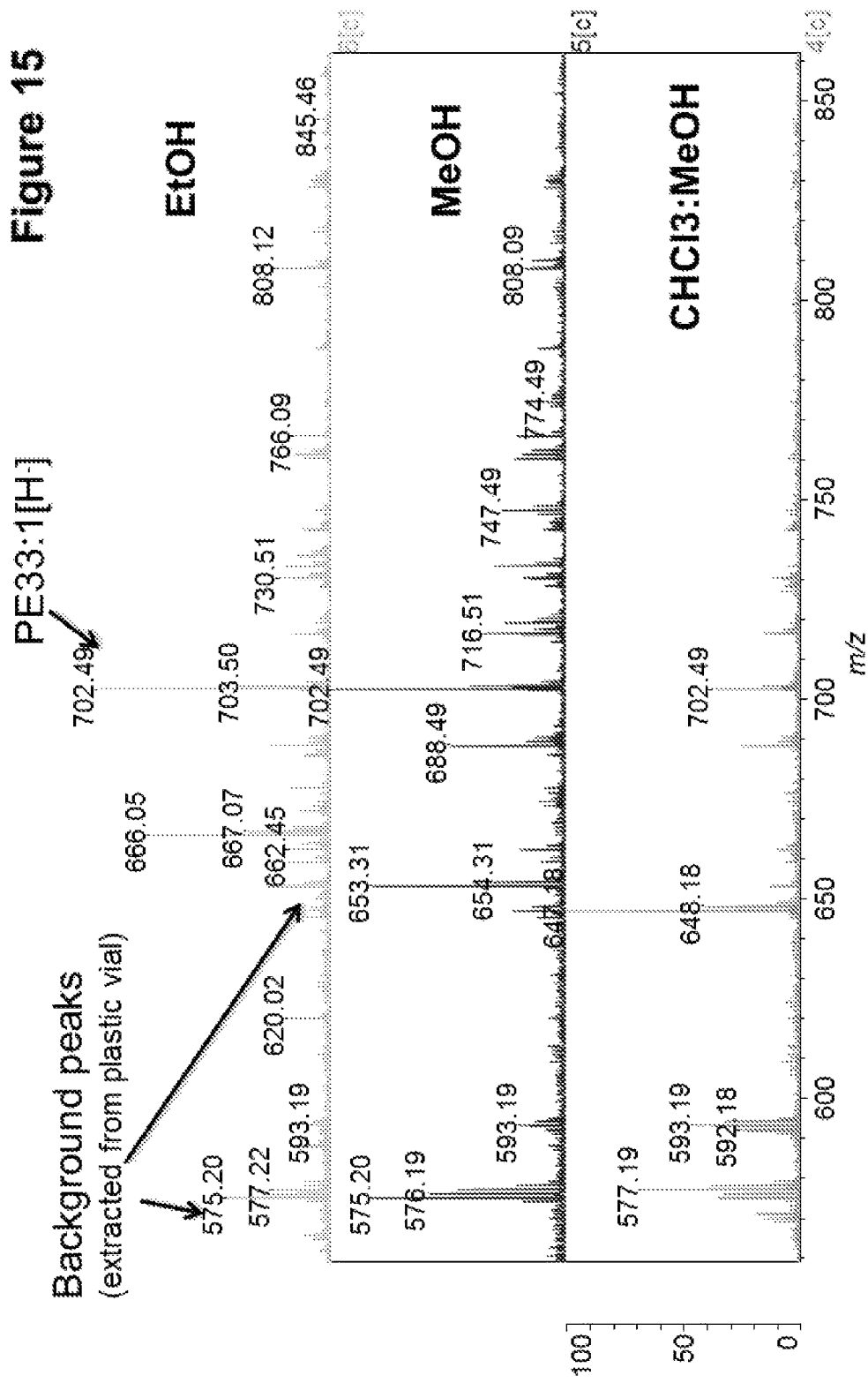

FIG. 15 shows (−)MALDI −MS spectra of *K. pneumoniae* using different extraction solvents (upper trace EtOH; middle trace MeOH; and lower trace Folch).

FIG. 16 shows protein typing results of *K. pneumoniae* and *E. Coli* using (A) extraction methods of the present application; and (B) directly from cell culture.

Figure 17:
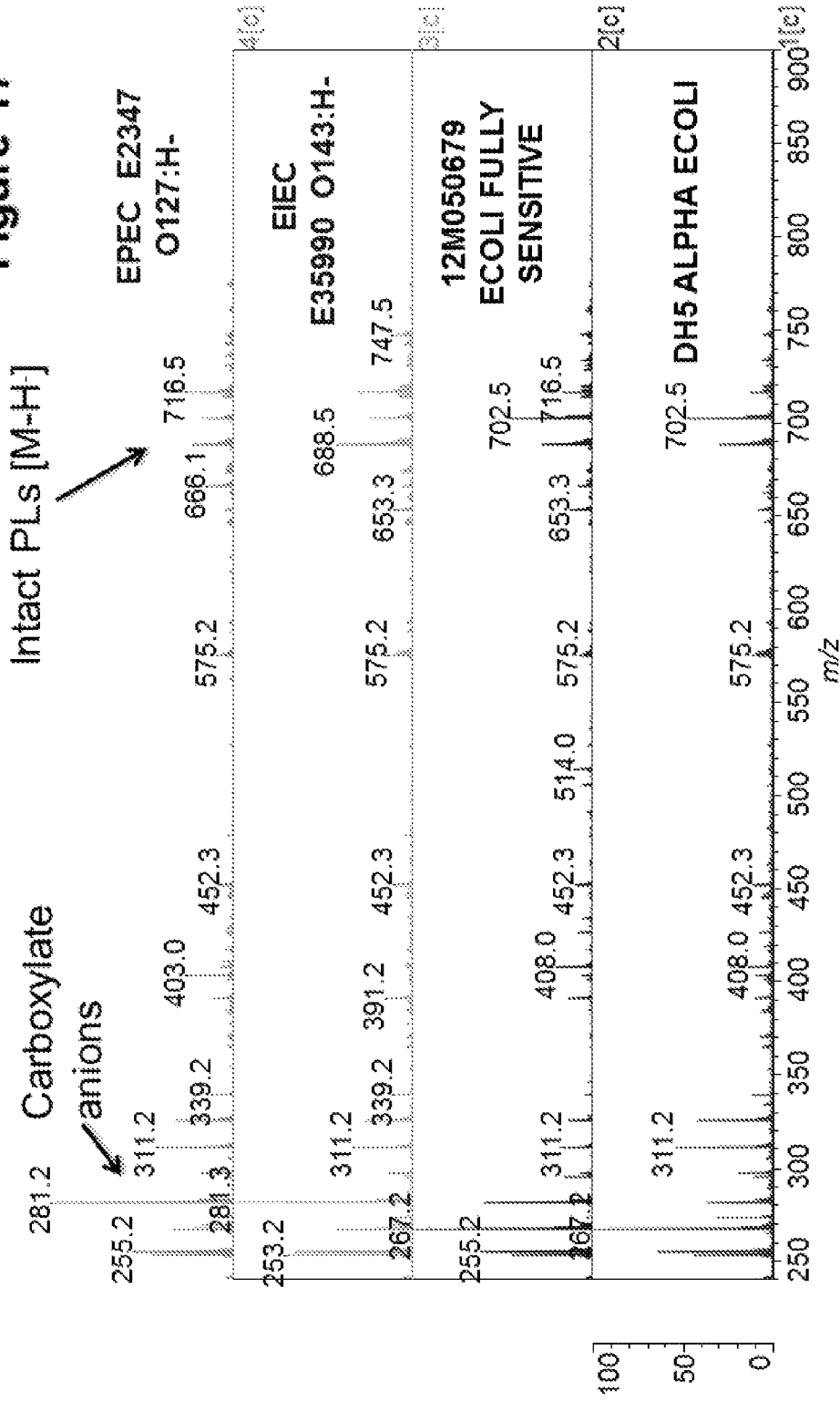

FIG. 17 shows (−)MALDI −MS spectra of different *E. coli* strains (using MALDI-QIT-TOF detection) (upper trace EPEC E2347; second trace EIEC E35990; third trace 12 M050679 [*E. Coli* fully sensitive]; and lower trace DH5 Alpha *E. Coli*).

Figure 18:
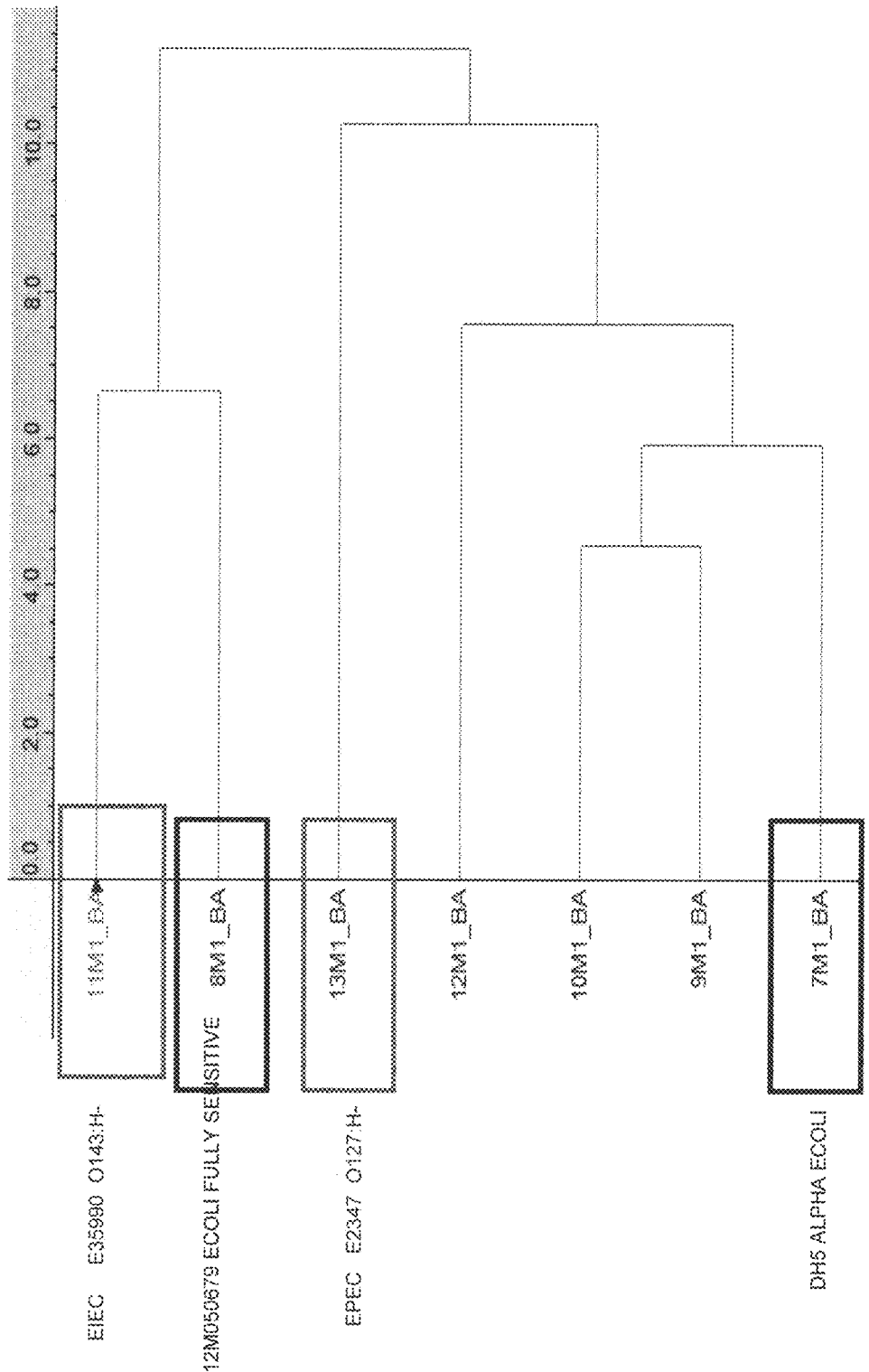

FIG. 18 shows (−)MALDI lipotyping cluster analysis (m/z 200-900 Selected Peaks).

Figure 19:
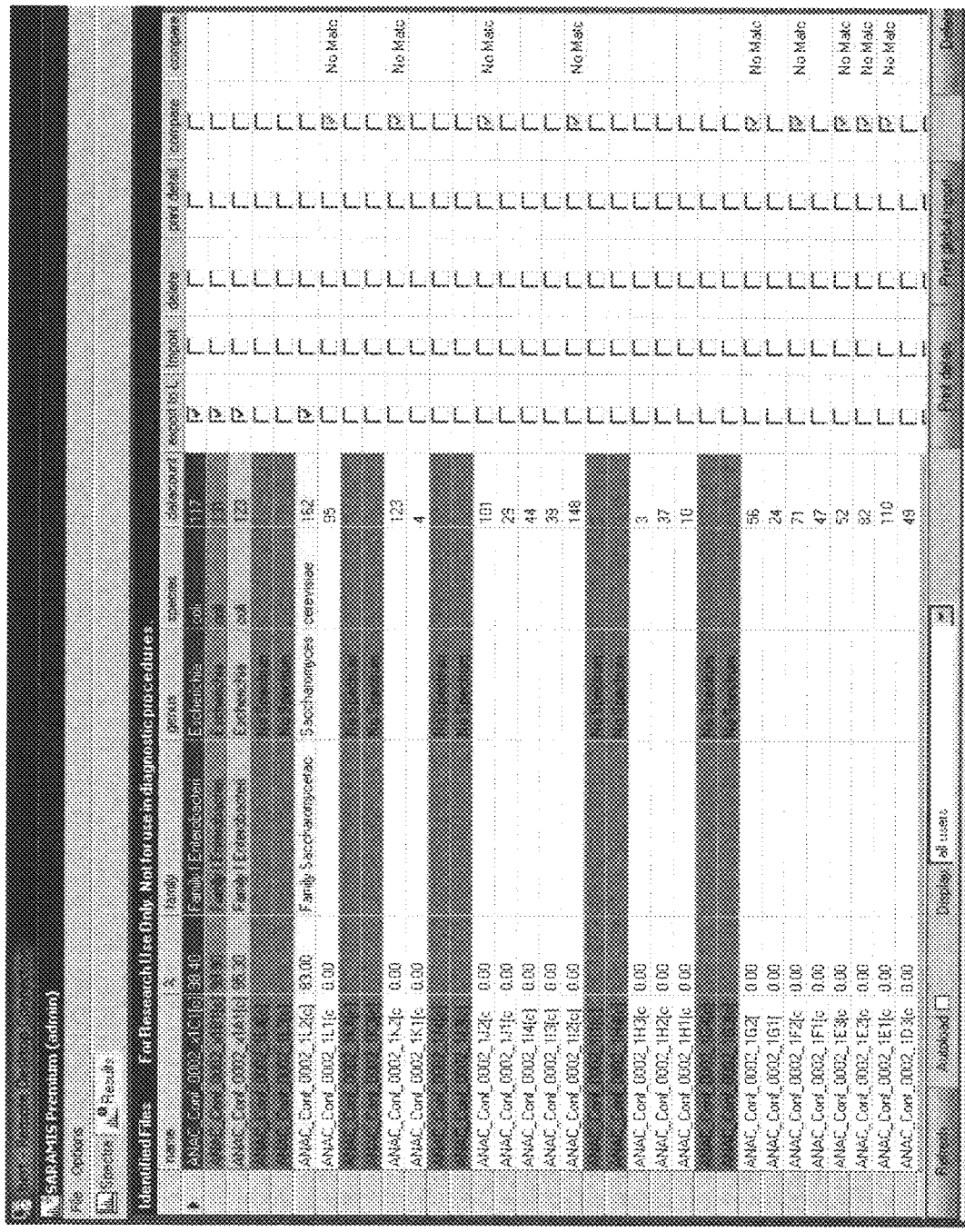

FIG. 19 shows protein typing results for yeasts and filamentous fungi (Saramis).

Figure 20:
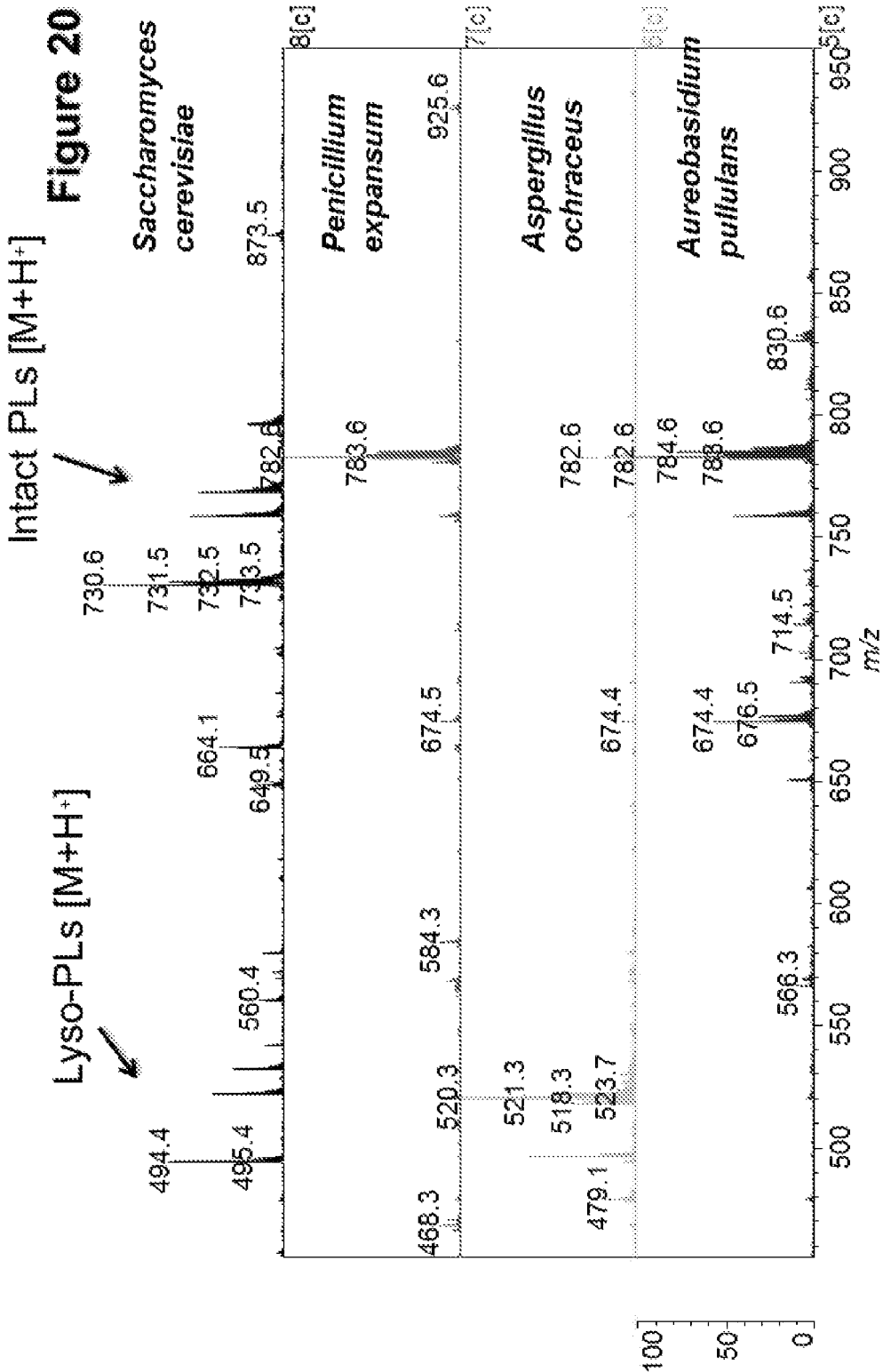

FIG. 20 shows (+)MALDI −MS spectra of different yeasts and fungi (using MALDI-TOF detection) (upper trace *Saccharomyces cerevisiae*; second trace *Penicillium expansum*; third trace *Aspergillus ochraceus*; and lower trace *Aureobasidium pullulans*).

Figure 21:
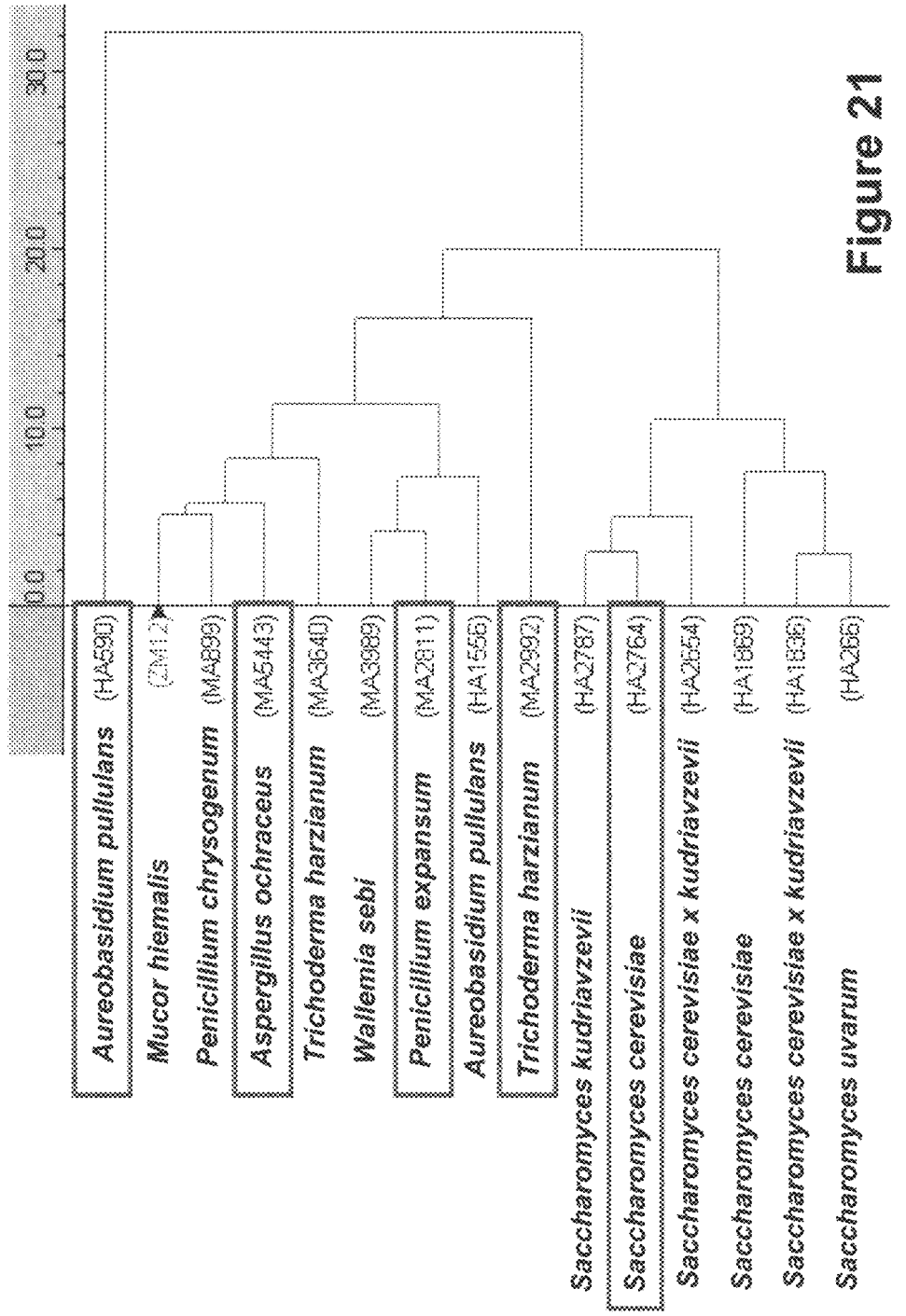

FIG. 21 shows (+)MALDI lipotyping cluster analysis.

Figure 22:
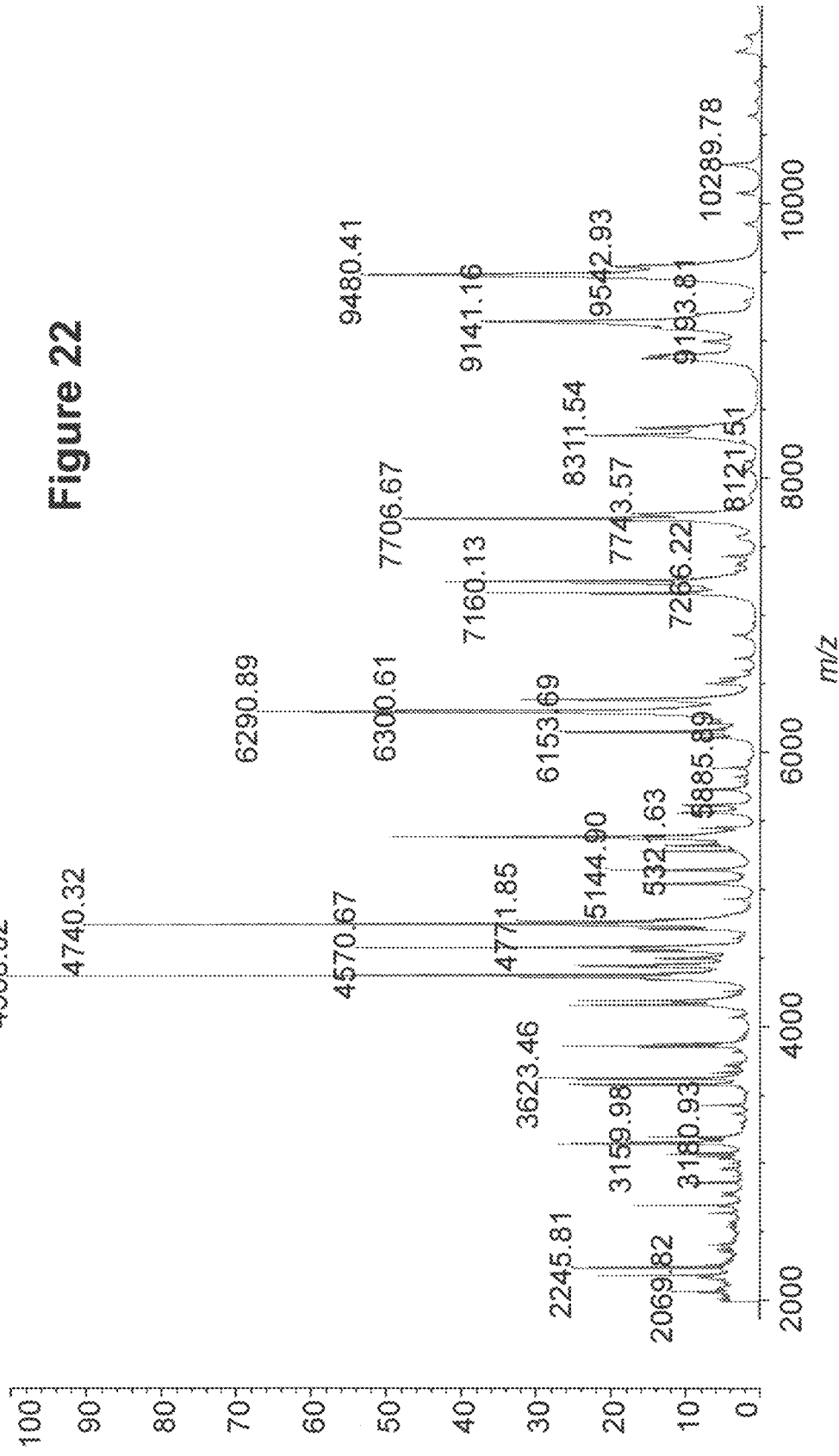

FIG. 22 shows MALDI-MS spectrum of *K. Pneumoniae* in the protein m/z range, corresponding to the protein analysis of FIG. 16.

FIG. 23 shows MALDI-MS spectrum of *E. Coli* DH5D in the protein m/z range, corresponding to the protein analysis of FIG. 16.

The embodiments described below are illustrative and by way of example only.

Methodology

Microbial Cell Cultures 13 different bacterial species and strains (listed in Table 1) were cultivated. The strains were grown overnight (24 hours) on Columbia blood (CB) agar or minimal medium (LB Agar, Sigma) in standard aerobic conditions at 37° C.

TABLE 1

Bacterial strains cultivated. Strains 6a and 6b are a mixed culture of *S. haemolyticus* and *C. Striatum*. Strains 7 and 8 are antibiotic sensitive, strains 9 and 10 are antibiotic resistant and strains 11, 12 and 13 are enteropathogenic *E. coli* strains. Antibiotic resistance was tested against 17 different compounds based on determination of the minimum inhibitory concentration (MIC) value.

| Strain number | Strain identification |
| --- | --- |
| 1 | ACTCC 22913 *S. aureus* |
| 2 | ACTCC 2912 *E. faecalis* |
| 3 | ACTCC 12228 *S. epidermis* |
| 4 | ACTCC 13047 *E. cloacae* |
| 5 | ACTCC 27853 *P. auruginosa* |
| 6a | 12M203885 *S. epi* |
| 6b | 12M206885 *C. striatum* |
| 7 | DH5 Alpha *E. coli* |
| 8 | 12M050679 *E. coli* (UPEC) |
| 9 | ACTCC 35218 *E. coli* |
| 10 | NCTC 13353 *E. coli* ESBL |
| 11 | E35990 (EIEC) |
| 12 | E60725 (EAEC) |
| 13 | E2347 (EPEC) |

9 yeas strains were also cultivated. They belong to *Saccharomyces cerevisiae* and *Saccharomyces kudriavzevii*, and were grown on a GYP (glucose, yeast extract, peptone) medium for three days at room temperature (25° C.).

Filamentous fungi (Hyphomycetes) were also cultivated. The fungi belong to *Aureobasidium, Aspergillus, Penicil-*

*lium, Trichoderma, Wallemia* and *Mucor*, and were grown on a Malt extract agar plate for one week at room temperature (25° C.).

Microbial Lipid Extraction

Three lipid extraction techniques were used.

In all three, a 10 μL plastic loop (Nunc) of pure bacterial cell culture (~$10^6$ cells) cultivated on either CB agar or LB Agar (Sigma) overnight at 37° C., was suspended in 500 μL of double distilled $H_2O$, vortexed shortly and centrifuged at 3000 g in a micro-centrifuge for 3 minutes. The supernatant was then removed leaving a bacterial cell pellet suspended in 40 μL of double distilled $H_2O$. This process was repeated once before lipid extraction was performed.

The same procedure was used in case of yeasts and filamentous fungi.

Method 1: Methanol Extraction

200 μl of MeOH (Sigma) was added to the suspended pellet. Microbial cell suspensions were then sonicated at room temperature for 5 minutes and subsequently placed on ice for 15 minutes. The suspensions were then vortexed for several seconds and placed on ice for a further 15 minutes to complete lipid extraction. The resulting suspension was then centrifuged at 12000 g for 5 minutes to precipitate the cell debris. The supernatant was then stored at −20° C. until MS analysis was performed.

Method 2: Acetone Extraction

200 μl of Acetone was added to the suspended microbial cell pellet. Bacterial suspensions were then placed on ice for 30 minutes. The resulting suspension was then centrifuged at 3000 g for 3 minutes. The supernatant was then stored at −20° C. until MS analysis was performed.

Method 2a: Methanol: Acetone Extraction

Various MeOH/Acetone mixtures were also tested for lipid extraction of yeasts and fungi and revealed equally suited to provide good mass spectral quality. The best mixtures ranged from 70:30 to 90:10 by volume.

Method 3: Chloroform/Methanol Extraction

300 μl of $CHCl_3$:MeOH=70:30 (v/v) was added to the suspended cell pellet then placed on ice for 30 minutes. 75 μl of 0.7M Formic acid was then added to the cell suspension and placed on ice for a further 15 minutes. The bacterial suspension was then vortexed for several seconds and placed on ice for a further 15 minutes in order to be separated into a aqueous upper and organic lower phase. Afterwards the cell suspension was centrifuged at 12000 g for 5 minutes and the lower phase containing the extracted lipids was aspirated with a pipette and transferred to a new sample vial. Finally the lipid extracts were stored at −20° C. until MS analysis was performed.

MALDI Sample Preparation

For the acquisition of MALDI lipid profiles different lipid class specific co-matrix systems were used.

2,4,6-trihydroxyacetophenone (THAP) dissolved in Acetone:Methanol (MeOH)=70:30 (v/v) containing 10 mM sodium (Na) acetate was used for detection of neutral lipids (e.g. DAGs, TAGs, DGDCs, etc.).

6-aza-2-thiotymine (ATT) dissolved in Ethanol (EtOH): $H_2O$=90:10 (v/v) containing 10 mM diammoniumhydrogen citrate (DAHC) was used for detection of cationic phospholipids (e.g. PC, SM).

9-aminoacridine (9AA) dissolved in Isopropanol:Acetonitrile (ACN)=60:40 (v/v) containing either 5 mM guanidine-HCl (GUA) or 0.5% pyridine (PYR) as matrix additives was used for detection of anionic PLs (e.g. PA, PE, PG, PS, PI, CL).

A small volume (e.g. 0.3-0.5 μL) of the matrices at a concentration of 10 g/L was spotted on the MALDI target surface immediately followed by an equal volume of the microbial lipid extracts. This known "dried droplet technique" is flexible and fully automatable sample application method for the analysis of lipids.[17]

FlexiMass™-DS (Shimadzu, Manchester, UK) 48-well disposable polymeric target slides were used as sample support because they provide optimal performance without producing any interfering background noise in the low mass range (i.e. m/z<1000) compared to conventional stainless steel targets.

After crystallization the samples were inserted into the MALDI mass spectrometer for immediate analysis using a specific target adaptor carrying up to four sample plates (AXIMA-Precision™, Shimadzu, Manchester, UK).

In the case of MALDI sample preparation for protein analysis, the matrix solution consists of 1 ml of a saturated CHCA solution in 33/33/33 acetonitrile/ethanol/water containing a final concentration of 3% TFA.

Preparation: Weigh out approximately 40 mg of CHCA. Dissolve in 1 mL 33/33/33 acetonitrile/ethanol/water containing a final concentration of 3% TFA (prepared previously). Mix using a vortex. At room temperature, this should result in a saturated solution; centrifuge or allow any undissolved solid to settle.

To analyse the mixture (Lipids+Protein pellets or Proteins pellet only): 1 μL of sample is transferred directly on to the MALDI target and 1 μL of the CHCA matrix solution (see above) is then added.

The MALDI analysis steps is the same as for lipid analysis except the mass range is different (2000-22000 Max) and in positive mode.

MALDI-MS Measurements

MALDI lipid profiles were acquired using a MALDI-reflectron-TOF (RTOF) mass spectrometer (AXIMA-CFR$^+$ or AXIMA-Performance, Shimadzu, Manchester, UK) equipped with a nitrogen laser (λ=337 nm) and an integrated monochrome video-image system (25× magnification) for direct observation of the target surface and matrix under investigation.

The ion accelerating voltage was set to 20 kV and the reflectron analyser was operated at 25 kV. Measurements were performed in the positive (+) or negative (−) ionization mode using delayed ion extraction for baseline monoisotopic mass resolution of the peaks.

The laser energy was adjusted to 10-20% above the threshold of laser irradiation (power 90-100) according to the manufacturer's nominal scale (power 180 at maximum), whereby a circular laser raster (~500-1000 μm diameter) adjusted to the morphology of the matrix spots on the target surface was used.

Microbial Identification

A hierarchical cluster analysis was performed in order to establish a dendrogramme displaying the relatedness of the different microbial species based on their lipid/protein profiles using the commercially available statistics software packages DataLab 3.5 (http://www.lohninger.com/datalab) and BioNumerics 7.1 (Applied Maths, Belgium). In case of DataLab the Euclidean distance measure was used and the Linkage type was based on the Ward's method.

Before statistical analysis the MALDI-MS data was processed. Firstly, MALDI data of each individual organism were exported as a so-called "mass list" containing m/z values and the corresponding signal intensity to Microsoft Excel 2007. Secondly, a data alignment based on ascending m/z values from all samples was performed and signals originating from the culture media (e.g. CB or LB agar), the plastic tubes used for the lipid extractions as well as matrix background signals (recorded from blank samples) were subtracted. This leads to a data matrix of m/z values and the corresponding signal intensity found within all samples. Thirdly, the signal intensities of all peaks for each organism were normalized to the sum of signals (i.e. displayed as % relative intensity) and imported into the software programmes for cluster analysis.

EXAMPLES

Example 1

Comparison of Extraction Solvents

Figure 1:
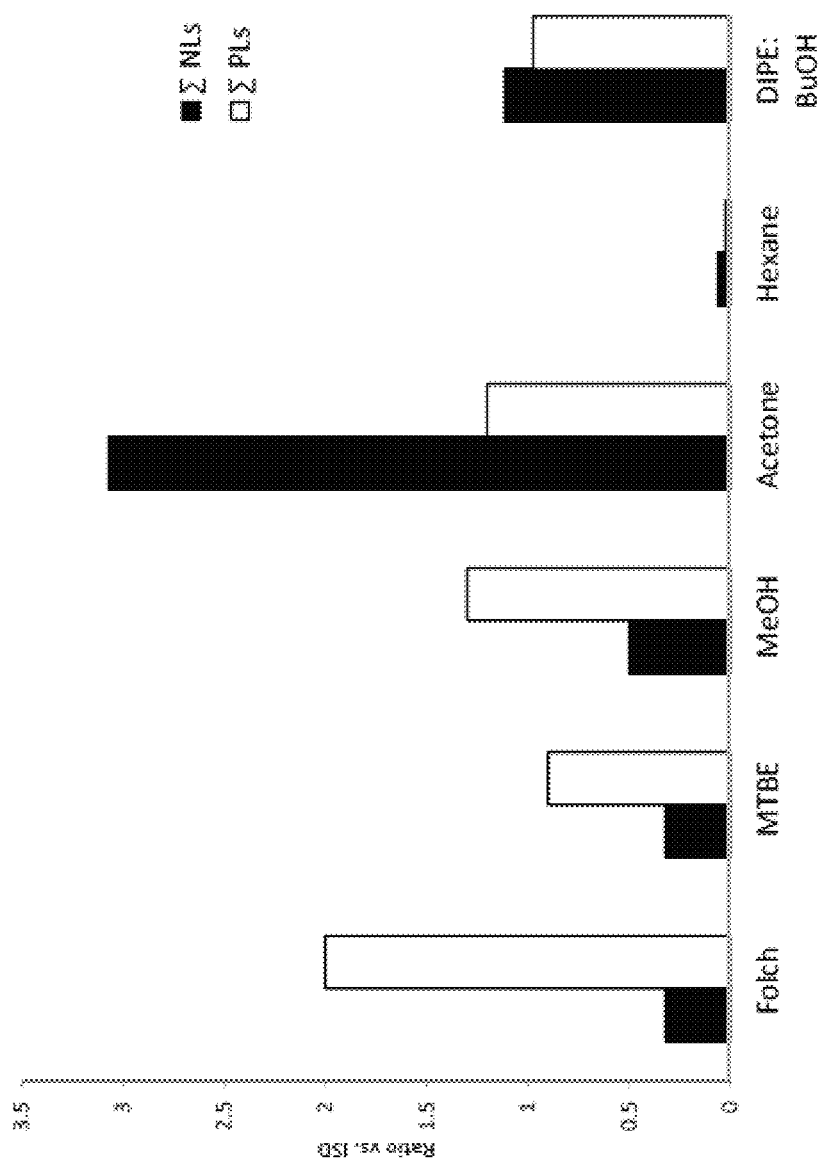

FIG. 1 shows the extraction efficiency of 6 different organic solvents, for both charged phospholipids (PLs) and neutral lipids (NLs). The extraction efficiency is calculated based on the signal intensity of the corresponding lipid species in a MALDI-MS spectrum.

It can be seen that Folch, MTBE and MeOH solvents preferentially allows detection of PLs, whereas acetone favours the detection of NLs. An almost equal efficiency for both lipid classes was observed using DIPE/BuOH while the worst results were obtained for Hexane.

Based on these preliminary results, Folch, MeOH and acetone were further evaluated for the use in the lipid extraction step and MALDI-MS analysis of the PLs from the different bacteria, yeasts and fungal species.

Figure 2:
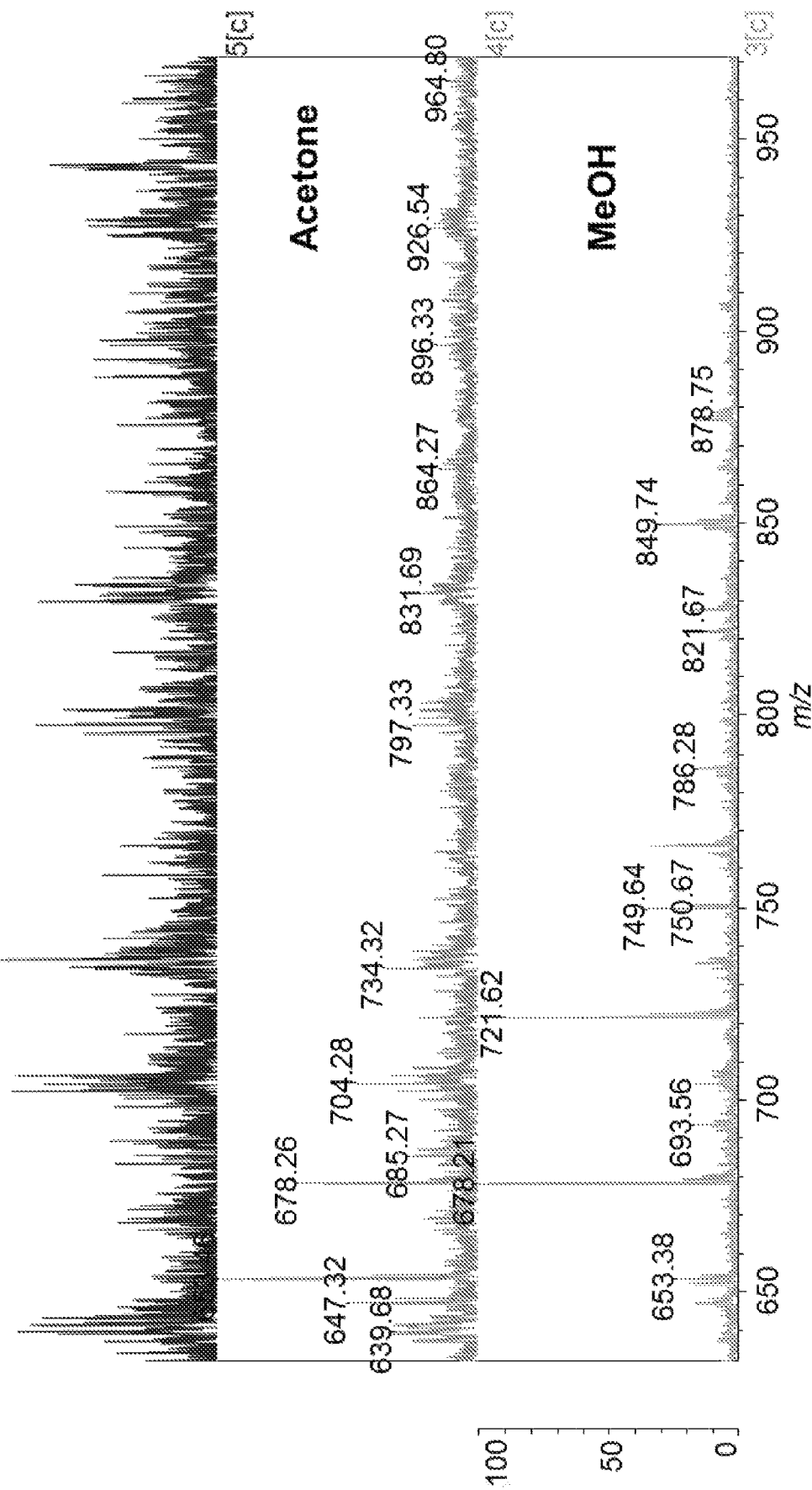
FIG. 2 shows three lipid MALDI-MS spectra obtained using three different lipid-extraction solvents applied to *S. aureus*, obtained in the negative ionisation mode (top trace=Folch, middle trace =acetone, and bottom trace=MeOH).

These three solvents were applied to a Gram+ bacterium (*S. aureus*). It can be seen from FIG. 2 that methanol returned a lipid MALDI-MS spectrum with the best signal-to-noise (S/N) ratio.

Example 2

Comparison of Matrix Substances

Figure 3:
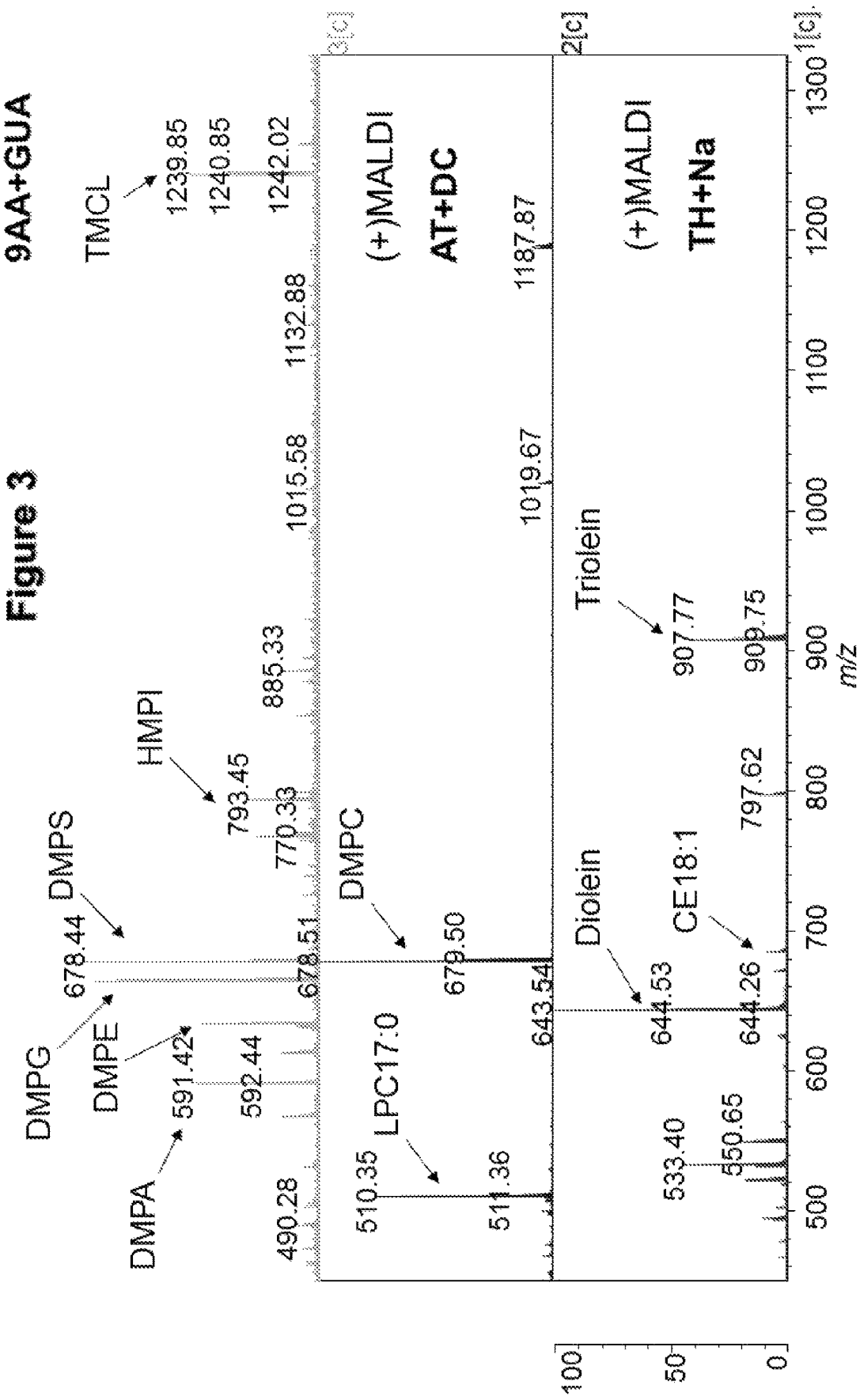
FIG. 3 shows three MALDI-MS spectra obtained using different matrix substances optimised for the detection of NLs (TRAP-Na matrix), cationic PLs (ATT-DC matrix) and anionic PLs (9AA-GUA matrix).

FIG. 3 shows three different mass spectra of the same lipid sample, containing a mixture of different lipid standards. The spectra were obtained using different matrix substances according to the method described above. It can be seen that in the negative mode, 9AA-GUA allows detection of a large number of peaks. These correspond to anionic phospholipids.

It can also be seen that both ATT and THAP return clear spectra in the positive mode. The ATT-DC spectrum peaks correspond to cationic phospholipids, and the THAP-Na peaks correspond to neutral lipids. It can be seen that in the positive mode, fewer peaks are detected.

The inventors assessed the selectivity of the three different matrix substances for ionization of the different major PL-classes present in biological membranes. The results are shown in FIG. 4.

The data show that in the positive mode, cationic PLs (PC and SM) from an equimolar PL-mixture are more readily ionised and detected than anionic PLs (e.g. PA, PE, PS), which were either not detectable or only showed weak signals (FIG. 2A). ATT shows the best ionisation across the range of PLs tested in the positive ionisation mode.

In contrast, in the negative mode the anionic PLs (e.g. PA, PE, PG, PS, PI, CL) were readily detectable, but PC and SM could not be detected (FIG. 2B). 9AA allowed an almost equal detection of all anionic PLs, whereas THAP and ATT showed prevalence for the ionization of PG and PS but not the other PL-classes.

Consequently, ATT and 9AA revealed the preferential matrix substances for microbial lipid profiling in (+) and (−) ionization mode respectively. These are the preferred matrix components.

Example 3

Effect of Culture Medium and Ionization Mode

FIG. 5 shows the mass spectrum obtained from blood agar in the presence of a methanol lipid-extraction solvent. Several background peaks are seen in the lipid profiling mass range (m/z 700-1500) when measured in the (+)MALDI mode, but not in the (−)MALDI mode.

This is because blood agar contains some plasma lipids (e.g. derived from blood cells and lipoproteins) which are mostly cationic PL-species (mainly LPC, PC, and SM), and which are therefore preferentially detected in the (+) ionization mode This problem can be circumvented in the (+)MALDI mode by using minimal medium (devoid of exogenous lipids) instead of blood agar. The resultant lipid mass spectrum is essentially the same, but with fewer culture medium contaminants. However, the use of minimal medium generally leads to less favourable culture conditions, and results in longer incubation times to obtain a sufficient number of cells for analysis. The (−) mode allows for blood agar to be used in cultivation, whilst minimizing signals from the agar.

Example 4

Detection of Fatty Acids

The negative ionization mode allows detection of carboxylate anions resulting from dissociation of fatty acid residues that make up lipids. This can aid in microbial identification, as different strains comprise different FAs.

FIG. 6A shows a lipid MALDI-MS spectrum obtained according to the claimed method for an *E. coli* strain. The inset shows 7 peaks which have been attributed to seven major FA-residues of the PLs recorded in the lipid extracts of *E. coli*.

Based on the assignment of the carboxylate ions to specific peaks of the lipid profile recorded in the MS1 mode, the FA-composition of all intact PLs detectable in the (−) mode can be calculated using tandem mass spectrometry.

FIG. 6B shows the MS2 spectrum obtained by low-energy collision-induced dissociation (CID) analysis of the three most abundant signals (m/z 688.5, 702.5, 716.5) from the mass spectrum of FIG. 6A (indicated by asterisks).

It can be clearly seen that each of the MS2 spectra contains only a selected number of the [RCOO]— ions detected in the MS1 mode. Based on this information the composition of the lipid species representing the three peaks could be identified as follows:

PE(16:0/16:1(9Z)), PE(17:1(9Z)/15:0) for m/z 688.5;
PE(16:0/17:1(9Z)), PE(17:0/16:1(9Z)) for m/z 702.5; and
PE(16:0/18:1(9Z)), PE(17:0/17:1(9Z)) for m/z 716.5.

These findings match previously published data on the lipid composition of *E. coli* obtained by (−)LC-ESI-MS/MS [18]. However, MALDI-MS analysis is simpler and quicker to perform.

Nevertheless, it should be noted that the exact structure of the FA-residues (including for example, chain-branching, cyclization or the position of double bonds) cannot be elucidated using low-energy CID (e.g. differentiation between cy17:0 or 17:1). To obtain this information the use of instruments allowing for high-energy MALDI-CID-MS/MS would be necessary[19].

Example 5

Reproducibility of Spectra

MALDI mass spectra were obtained by the claimed method of 9 different yeast strains belonging to Saccharomyces cerevisiae and Saccharomyces kudriavzevii.

The lipid composition of S. cerevisiae is well known[20]. The peaks obtained by different spectra could therefore be readily assigned to particular lipids.

The reproducibility of the individual species within MALDI lipid profiles was measured as the relative signal intensity variation (RSIV) determined from the coefficient of variation (CV) of the individual peaks from NLs and PLs recorded from 4 independent sample preparations of the same organism using THAP, ATT and 9AA matrix in the (+) and (−)MALDI mode. See FIGS. 12A to 12C.

- The RSIV of the NL-profile represented by 14 peaks related to the major diacylglycerol (DAG) and triacylglycerol (TAG) molecular species of S. cerevisiae shows a mean CV of 10.4±5.2.
- The RSIV of the cationic PL-profile represented by 25 peaks related to the major lyso-phosphatidylcholine (LPC) and phosphatidylcholine (PC) molecular species shows a mean CV of 13.2±7.9.
- The RSIV of the anionic PL-profile represented by 24 peaks related to the major phosphatidic acid (PA), lyso-phosphatidylethanolamine (LPE), phosphatidylethanolamine (PE), phosphatidylglycerol (PG) and phosphatidylinositol (PI) molecular species shows a mean CV of 15.8±10.8.

These data are in the range of routine analytical system errors. Thus, the spectra are highly reproducible, and the claimed method meets the requirements to be used for microbial diagnostics reliably.

Example 6

Differentiation of 4 Different Microbe Types 4 microbes were subjected to methanol lipid extraction. These were:
1. S. aureus—gram+ bacteria
2. E. coli—gram− bacteria
3. Sacchoaromyces sp—yeast
4. Penicillium sp.—filamentous fungi Each of the lipid extracts was separately incorporated into ATT matrix, and a MALDI-MS spectrum was obtained in the positive mode. The results are shown in FIG. 7A.

Each of the lipid extracts was also separately incorporated into 9AA matrix, and a MALDI-MS spectrum was obtained in the negative mode. The results are shown in FIG. 7B.

A visual inspection of the MALDI mass spectra clearly indicates that the microbes can be differentiated. A cluster analysis on the basis of the (+) and (−)MALDI lipid profiling data comprising 60-80 selected lipid related peaks recorded in the mass range between m/z 400-1000 (up to 1500 in the negative mode) demonstrates a very good differentiation of the different microbial species. See FIGS. 8A and 8B.

The classification of the different microorganisms based on cluster analysis was essentially identical for both the (+) and (−)MALDI mode lipid profiles. This observation indicates that the use of only one ionization mode is sufficient for reliable microbial differentiation.

Example 7

Differentiation of Bacteria at the Strain Level

E. coli represents a diverse group of Gram-bacteria closely related to other species (e.g. Enterobacter, Shigella, Salmonella, Klebsiella, etc.) belonging to the family of the "Enterobacteriaceae", which typically live in the intestine of warm-blooded organisms (e.g. different mammalian species including humans).

The 13 bacteria strains listed in Table 1, including antibiotic resistant, antibiotic sensitive and pathogenic E. coli strains, were analysed according to the method described above.

FIG. 9 shows the (−)MALDI mass spectra displayed in the m/z range 240-400 and 650-800 of four E. coil strains.

Differences between the MALDI-MS spectra are plainly apparent. In particular, the profiles for strains #7 and #8 (i.e. the two sensitive to antibiotics) are distinctly different to the profiles of strains #11 and #13 (i.e. the resistant strains).

Inspection of the FA-profile (i.e. based on detection of the [RCOO]— ions) by MALDI-QIT-TOF-MS/MS (FIG. 9A) shows that these differences can mainly be attributed to a different content of 17:1 (cy17:0) and 18:1 representing the major FA residues of the peaks at m/z 702 and 716 (FIG. 9B) indicated by circles.

Cluster analysis of all the species displayed in Table 1 shows a differentiation of two major groups represented by;
(1) Gram+ bacteria S. aureus (#1), S. epidermidis (#3) and a mixed culture of S. haemolyticus and C. striatum (#6); and
(2) Gram−Enterobacteriaceae with three subclusters of the E. coli strains and related species (e.g. P. aeruginosa and E. faecalis).

See FIG. 10.

Thereby, the antibiotic sensitive strain (#7) can be clearly differentiated from the antibiotic resistant strains (#9, #10) and the enteropathogenic strains EIEC (#11), EAEC (#12) and EPEC (#13), respectively.

In the cluster analysis, the fully sensitive uropathogenic (UPEC) E. coil 12M050679 strain (#8) was found with P. aeruginosa and E. faecalis in the even more distant cluster.

The same data set was also subjected to a cluster analysis using another software tool (BioNumerics) and the results were very similar. This indicates that the approach is robust.

Display of the results in the form of a so-called "minimal spanning tree" (MST) shows the relative relatedness of the different bacteria analysed during our study (See FIG. 11).

Additional Examples and Analysis

FIG. 13 shows an "all-in-one" microorganism identification approach (lipid fingerprinting and protein fingerprinting of the same microbes) utilising a rapid single-step extraction (~5-10 min dependent on the rigidity of the cell wall structure) using MeOH or EtOH and ultrasonication. Thereby, a homogenous suspension of hydrophilic and hydrophobic molecules (i.e. mainly cellular proteins and membrane lipids) is formed. This allows the simultaneous analysis of both proteins and lipids by using the most suitable MALDI matrix systems (e.g. CHCA for proteins; ATT or 9AA for lipids) and MALDI-MS analysis in positive and/or negative mode. Finally, the obtained MS data are searched against a database using bioinformatic software tools (e.g. multivariate data analysis).

Compared to known protocols for cell extraction (e.g. Bruker) it is much less time consuming and sensitive as it avoids extensive washing, extracting, drying and resuspension steps with the risk for sample losses and modification (e.g. artificial oxidation and degradation).

This approach represents a significant improvement over existing protocols focussing only on protein patterns for identification (i.e. MALDI proteintyping) by expanding the effective mass range of analysis from 2-20 kDa to 0.2-20 kDa and incorporating the information content of different types of molecules (e.g. proteins and lipids).

FIGS. 14 and 15 show the improvements of the single-step extraction for lipid analysis of bacteria by MALDI-MS. Using the ultrasonication extraction protocol high-quality mass spectra from Gram- (FIG. 14A) and Gram+ (FIG. 14B) bacteria can be obtained in shorter time than using conventional protocols (5 minutes ultrasonication vs. 30 minutes on ice with vortexing) which makes it more suitable for routine work (e.g. in clinical labs). Moreover, additional lipid species (e.g. Lysyl-PG from *S. aureus*) become detectable which increases the information content of the analysis. The use of e.g. MeOH or EtOH improves the quality of mass spectra (FIGS. 15A and 15B) and reduces the contribution of background signals (e.g. "plastic peaks") compared to conventional solvents (e.g. $CHCl_3$) used for lipid extraction (FIG. 15C).

FIGS. 16 to 18 demonstrate advantages of the "all-in-one" approach for the identification of bacteria. In FIG. 16 the SARAMIS search results of different *E. coli* and *K. pneumoniae* strains are shown. It can be seen that the confirmation level based on % ID and the data count (SCORE) was essentially higher using the single-step extraction protocol ((A) blue, top set, extraction=MeOH) compared to direct cell analysis from the culture plate ((B) red, lower set). The differences were especially visible in case of *K. pneumoniae* which contains a more rigid cell wall compared to *E. coli*. This clearly demonstrates the advantage of our method for proteintyping. Using additionally the information content of the lipid mass spectra based on the detection of fatty acids (i.e. carboxylate anions) and intact phospholipids (PLs) in the negative mode (FIG. 17) a clear differentiation of the *E. coli* strains was obtained based on hierarchical cluster analysis (FIG. 18). This allowed a differentiation of two pathogenic (red upper box EIEC E35990, and third box EPEC E2347) from non-pathogenic (black second box 12M050679 *E. Coli* fully sensitive, and lower box DH5 Alpha *E. Coli*) strains which could not be achieved based on proteintyping (SARAMIS) alone (FIG. 16).

This demonstrates the added value of the MALDI lipotyping for the identification of very closely related bacterial species.

FIGS. 19 to 21 demonstrate the advantages of the "all-in-one" approach for the identification of fungi. In FIG. 19 the SARAMIS search results of different yeasts and filamentous fungi are shown. It can be seen that the confirmation level (column headed "%") (even after protein extraction of the cells) was either very bad or that in many cases no useful mass spectrum for identification was available. This demonstrates the general problem of proteintyping for the identification of yeasts and especially filamentous fungi which contain more rigid cell wall structures compared to most of the bacteria. In contrast, using the lipid mass spectra in the positive mode following the single-step extraction protocol (FIG. 20) a nice differentiation of the yeasts (e.g. *Saccharomyces*) and different filamentous fungi (e.g. *Aspergillus, Penicillium, Trichoderma*, etc.) was obtained (FIG. 21).

FIGS. 22 and 23 show the protein m/z range for the samples corresponding to the protein analysis of FIG. 16. Good signal to noise and peak resolution facilitates high confidence levels (% value in FIG. 16).

Regarding merging of data sets for the mass spectrometry data for lipid components and for the protein components of a given microbe, the present inventors have acquired a protein mass spectrum of *Saccharomyces cerevisiae* (using a CHCA matrix) and a lipid mass spectrum of the same microbe (using a ATT matrix) and then combined/merged them. Specifically, by combining lipid data from the m/z range of 500 to 900 with protein data from the m/z range of 2000 to 15000 a merged data set in the m/z range 500 to 15000 was obtained. Cluster analysis based on this merged mass data enabled strain-level identification.

These results demonstrate the advantage of the combined lipid and protein extraction and analysis approach for the identification of fungi. In this and other cases (e.g. bacterial and fungal spores, mycobacteria, lipid-enveloped viruses, etc.) where conventional proteintyping is compromised by the lack of proper protein extraction and/or lack of informative protein profiles MALDI lipotyping shows the potential to serve as a novel stand-alone tool for microbial identification.

REFERENCES

A number of publications are cited above in order to more fully describe and disclose the invention and the state of the art to which the invention pertains. Full citations for these references are provided below. The entirety of each of these references is incorporated herein.

[1] J. E. Cronan Ann. Rev. Microbiol. 2003, 57, 203-224
[2] W. Dowhan Ann. Rev. Biochem. 1997, 66, 199-232
[3] Y-M. Zhang and C. O. Rock J Lipid Res, 2009, 50, S115-S119.
[4] A. J. De Siervo J. Bacteriol. 1969, 100, 1342-1349
[5] L. O. Ingram Appl. Environ. Microbiol. 1977, 33, 1233-1236
[6] K. Lahtchev et al. Tome 2000, 53, 75-78
[7] Y. Koga Archaea 2012, 1-6
[8] Able K., De Schmertzing H., Peterson J. I. J., Bacteriol. 1963, 85, 1039-1044
[9] W. W. Christie Lipids 1998, 33, 343-353
[10] J. E. Cronan Ann. Rev. Microbiol. 2003, 57, 203-224
[11] D. N. Heller, R. J. Cotter, C. Fenselau, et al. Anal. Chem. 1987, 59, 2806-2809
[12] P. B. W. Smith et al. Anal. Chem. 1995, 67, 1824-1830
[13] V. Havlicek et al. Anal. Chem. 2013, 85, 790-797.
[14] J. Gidden et al. Int. J. Mass Spectrom. 2009, 283, 178-184
[15] X. Shu et al. Int. J. Mass Spectrom. 2012, 321/322, 71-76
[16] D. F. Welch Clin Microbiol Rev. 1991, 4, 422-438
[17] G. Stübiger and O. Belgacem *Anal Chem.* 2007, 79, 3206-3213.
[18] D. Oursel et al. Rapid Commun Mass Spectrom. 2007, 21, 1721-1728
[19] E. Pittenauer and G. Allmaier J Am Soc Mass Spectrom. 2009, 20, 1037-1047
[20] C. S. Ejsing et al. Proc Natl Acad Sci USA 2009, 106, 2136-2141

The invention claimed is:

1. A method of analysing microbes, the method comprising:
   i) a single extraction step, comprising addition of an organic extraction composition to the microbes to provide extracted material comprising both lipids and proteins, ii) a sample preparation step, comprising preparation of at least one MALDI sample of lipid analysis incorporating the extracted material and at least one MALDI sample for protein analysis incorporating the extracted material;

iii) a data gathering step, comprising performing MALDI-based mass spectrometry on the at least one MALDI sample for lipid analysis so as to obtain mass spectrometry data on the lipid composition of the microbes and on the at least one MALDI sample for protein analysis so as to obtain mass spectrometry data on the protein composition of the microbes; and iv) a microbe identification step, comprising analysis of the mass spectrometry data to identify microbial strain.

2. A method according to claim 1, wherein the mass spectrum data for the lipids and the mass spectrum data for the proteins is merged.

3. A method according to claim 1, wherein the at least one MALDI sample for lipid analysis comprises 9AA matrix material.

4. A method according to claim 3, wherein the at least one MALDI sample for lipid analysis comprises guanidine-HCl or pyridine.

5. A method according to claim 3, wherein in the data gathering step the at least one MALDI sample for lipid analysis is negatively ionised.

6. A method according to claim 1, wherein the at least one MALDI sample for lipid analysis comprises ATT matrix material.

7. A method according to claim 6, wherein the at least one MALDI sample for lipid analysis comprises DAHC.

8. A method according to claim 6, wherein in the data gathering step the at least one MALDI sample for lipid analysis is positively ionised.

9. A method according to claim 1, wherein in the data gathering step, the m/z range over which data is obtained on the lipid composition of the microbes is from about 100 to about 3000.

10. A method according to claim 1, wherein in the at least one MALDI sample for protein analysis comprises CHCA matrix material.

11. A method according to claim 1, wherein in the data gathering step, the m/z range over which data is obtained on the protein composition of the microbes is from about 2000 to about 20000.

12. A method according to claim 1, wherein in the data gathering step, the MALDI-based mass spectrometry uses one or more of the following techniques:
 a) Quadrupole ion trapping (QIT);
 b) Time of flight measurement (TOF);
 c) Reflection time of flight measurement (RTOF);
 d) Orbitrap mass spectrometry;
 e) Fourier transform mass spectrometry (FTMS);
 f) Tandem mass spectrometry (MS/MS); and
 g) Collision induced dissociation.

13. A method according to claim 1, wherein in the sample preparation step, the one or more MALDI samples are prepared on a polymeric or plastics MALDI sample plate.

14. A method according to claim 1, wherein in the microbe identification step, the mass spectrometry data is compared with known values to identify the microbe.

15. A method according to claim 1, wherein in the microbe identification step, hierarchical cluster analysis is carried out on the mass spectrometry data.

16. A method according to claim 1, wherein the extraction step extracts phospholipids.

17. A method according to claim 1, wherein the extraction step extracts neutral lipids.

18. A method according to claim 1, wherein the organic extraction composition comprises less than 1 vol % halogenated organic solvent.

19. A method according to claim 1, wherein the organic extraction composition comprises more than 50 vol % alcohol or ether.

20. A method according to claim 1, wherein the organic extraction composition comprises more than 70 vol % methanol or ethanol.

* * * * *